(12) United States Patent
Fabene et al.

(10) Patent No.: US 7,682,613 B2
(45) Date of Patent: Mar. 23, 2010

(54) ANTI-LEUKOCYTE RECRUITMENT THERAPY FOR THE TREATMENT OF SEIZURES AND EPILEPSY

(75) Inventors: Paolo Francesco Fabene, Villafranca di Verona (IT); Eugene C. Butcher, Portola Valley, CA (US); Gabriela Constantin, San Floriano (IT)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/811,245

(22) Filed: Jun. 6, 2007

(65) Prior Publication Data

US 2008/0025992 A1 Jan. 31, 2008

Related U.S. Application Data

(60) Provisional application No. 60/811,873, filed on Jun. 7, 2006.

(51) Int. Cl.
*A61K 39/395* (2006.01)
*A61K 49/00* (2006.01)
*C07K 16/00* (2006.01)

(52) U.S. Cl. .................. 424/139.1; 424/9.1; 530/387.1

(58) Field of Classification Search ........................ None
See application file for complete search history.

(56) References Cited

U.S. PATENT DOCUMENTS 7,211,252 B2 5/2007 Mundy et al.
7,387,777 B2 6/2008 Wagner et al.

OTHER PUBLICATIONS

Löscher W., Epilepsy Research, 50(1-2): 105-123, Jun. 2002.*
Doggrell SA, Expert Opinion in Pharmacotherapy, 4(6):999-1001, 2003.*
Poser and Brinar, Epilepsy and Behavior, 4: 6-12, 2003.*
Sokic et al. Epilepsia, 42(1): 72-79, 2001.*
Duncan, "MRI studies. Do seizures damage the brain?", Prog. Brain Res., 2002, 135:253-261.
Duncan, "Seizure-induced neuronal injury: human data", Neurology, 2002, 59(9 Suppl 5):S15-S20.
Gall et al., "Integrins, synaptic plasticity and epileptogenesis", Adv Exp Med Biol., 2004, 548:12-33.
Holmes, "Seizure-induced neuronal injury: animal data", Neurology, 2002, 59(9 Suppl 5):S3-S6.
Holmes et al., "Seizure-induced damage in the developing human: relevance of experimental models", Prog. Brain Res., 2002, 135:321-334.
Parfenova et al., "Epileptic seizures cause extended postictal cerebral vascular dysfunction that is prevented by HO-1 overexpression", Am J Physiol Heart Ciro Physiol, 2005, 288(6):H2843-H2850.
Plata-Salaman et al., "Kindling modulates the IL-1beta system, TNF-alpha, TGF-beta1, and neuropeptide mRNAs in specific brain regions", Brain Res. Mol. Brain Res., 2000, 75(2):248-258.
Vezzani et al, "Functional role of proinflammatory and anti-inflammatory cytokines in seizures", Adv Exp Med Biol., 2004, 548:123-133.
Yabuuchi et al., "In situ hybridization study of interleukin-1 beta mRNA induced by kainic acid in the rat brain", Brain Res. Mol. Brain Res., 1993, 20(1-2):153-161.
John et al., "Discovery of a potent nanoparticle P-selectin antagonist with anti-inflammatory effects in allergic airway disease", The FASEB Journal, Dec. 2003, 17(15):2296-2298.

* cited by examiner

*Primary Examiner*—John D Ulm
*Assistant Examiner*—Stacey MacFarlane
(74) *Attorney, Agent, or Firm*—Bozicevic Field & Francis LLP; Pamela J. Sherwood

(57) ABSTRACT

Methods are provided for the prevention and treatment of seizures and epilepsy. It is shown herein that leukocyte recruitment plays a key role in the pathogenesis of epilepsy. Treatment with an agent that inhibits leukocyte recruitment has therapeutic and preventative effects in blocking recurrent seizures and epilepsy.

1 Claim, 15 Drawing Sheets

ANTI-LEUKOCYTE RECRUITMENT THERAPY FOR THE TREATMENT OF SEIZURES AND EPILEPSY

CROSS-REFERENCE TO RELATED APPLICATIONS

This applications claims benefit of priority to US provisional application 60/811,873, filed Jun. 7, 2006, which is herein incorporated by reference.

This invention was made with Government support under contract A147822 and GM37734. The government has certain rights in this invention.

BACKGROUND OF THE INVENTION

A seizure is a paroxysmal event due to abnormal, excessive, hypersynchronous discharges from an aggregate of central nervous system (CNS) neurons, while epilepsy is a condition in which a person has recurrent seizures due to a chronic, underlying process. Experimental and clinical data indicate that the occurrence of repeated seizures can lead to an epileptic condition. It is therefore of great interest to identify possible pharmacological treatments for seizures, and the time-frame in which such treatment is effective.

Epilepsy is a brain disorder characterized by, periodic and unpredictable seizures caused by the rhythmic firing of large groups of neurons. The behavioral manifestations of epileptic seizures in human patients range from mild twitching of an extremity to loss of consciousness and uncontrollable convulsions. Up to 1% of the population is afflicted, making epilepsy one of the most common neurological problems. The abnormal activity associated with epilepsy generates plastic changes in cortical circuitry that play a part in the pathogenesis of the disease. The importance of synaptic plasticity in epilepsy is indicated most clearly by an animal model of seizure production called "kindling." Over a period of time, a weak stimulus that initially had no effect will eventually cause full-blown seizures. This phenomenon is essentially permanent; even after an interval of a year; the same weak stimulus will again trigger a seizure.

Research has focused on where seizures originate and the mechanisms that make the affected region hyperexcitable. Evidence suggests that abnormal activity in cerebral cortex foci provide the triggers for a seizure that then spreads to other synaptically connected regions. Epileptic seizures can be caused by a variety of acute or congenital factors, including cortical damage from trauma, stroke, tumors, congenital cortical dysgenesis, and congenital vascular malformations.

No effective prevention or cure exists for epilepsy. Pharmacological therapies that successfully inhibit seizures are based on two general strategies. One approach is to enhance the function of inhibitory GABAergic synapses; the other is to limit action potential firing by acting on voltage-gated $Na^+$ channels. Commonly used antiseizure medications include carbamazepine, phenobarbital, phenytoin, and valproic acid. These agents must be taken daily, and only inhibit seizures in 60-70% of patients.

A number of processes are thought to contribute to the development of epilepsy including enduring increases in excitatory synaptic transmission, changes in GABAergic inhibition, neuronal cell death and the development of aberrant innervation patterns in part arising from reactive axonal growth. It has also been suggested that activities of integrin class adhesion receptors play roles in each of these processes by stabilizing activity-induced increases in synaptic strength and excitability. These same adhesion proteins and proteases play critical roles in axonal growth and synaptogenesis including processes induced by seizure in adult brain (Gall et al. (2004) Adv Exp Med Biol. 548:12-33).

REFERENCES

Holmes (2002) Seizure-induced neuronal injury: animal data. *Neurology* 59, S3-S6; Holmes et al. (2002) Seizure-induced damage in the developing human: relevance of experimental models. *Prog. Brain Res.* 135, 321-334; Duncan (2002) Seizure-induced neuronal injury: human data. *Neurology* 59, S15-S20; Duncan (2002) MRI studies. Do seizures damage the brain? *Prog. Brain Res.* 135, 253-261.

Parfenova et al. (2005) Epileptic seizures cause extended postictal cerebral vascular dysfunction that is prevented by HO-1 overexpression. *Am J Physiol Heart Circ Physiol* 288, H2843-H2850; Yabuuchi et al. (1993) In situ hybridization study of interleukin-1 beta mRNA induced by kainic acid in the rat brain. *Brain Res. Mol. Brain Res.* 20, 153-161; Plata-Salaman et al. (2000) Kindling modulates the IL-1beta system, TNF-alpha, TGF-beta1, and neuropeptide mRNAs in specific brain regions. *Brain Res. Mol. Brain Res.* 75, 248-258; Vezzani et al. (2004) Functional role of proinflammatory and anti-inflammatory cytokines in seizures. *Adv. Exp. Med. Biol.* 548,123-133 (2004).

SUMMARY OF THE INVENTION

Methods are provided for the prevention and treatment of seizures and epilepsy. It is shown herein that leukocyte recruitment plays a key role in the pathogenesis of epilepsy. Treatment with an agent that inhibits leukocyte recruitment has therapeutic and preventative effects in blocking recurrent seizures and epilepsy. It is shown herein that inhibition of leukocyte recruitment through a variety of adhesion molecules interferes with the pathogenesis of epilepsy, where the exemplary adhesion molecules include VLA-4; VCAM-1, LFA-1, ICAM-1 and PSGL-1.

In some embodiments of the invention the therapeutic agent blocks the interaction between leukocytes and adhesion molecules present on endothelial cells. Such agents include, without limitation, agents that block adhesion molecules involved in leukocyte trafficking and present on leukocytes or endothelial cells, for example integrins, selectins, mucins, which may be, without limitation, ICAM-1, VCAM-1, beta-2 integrins, VLA-4, P-selectin, L-selectin, E-selectin, PSGL-1, etc.

Confocal microscopy shows exogenous (F) and endogenous (E) migrated Gr1-positive cells. Fluorescence-labeled PMNs (exogenous cells) were injected 2 h post SE and in vivo homing of exogenously administered lasted 24 h. CD3-positive cells were detected both inside blood vessels (G) and perivascularly (H). Scale bars: (A) 100 µm; (D) 25 µm; bottom rectangle in (D): 8 µm; (E-H) 25 µm.

FIG. 3A-G. Alpha4 integrins mediates leukocyte recruitment after seizures. A, B. The behavior of PMNs and lymphocyte subpopulations was studied at 6 h and 24 h post-SE Cells were CMFDA-labeled or CMTMR-labeled. The number of venules and animals per group is provided at Table 3 and 4. Mean±SEM are shown. PLNs, peripheral lymph node cells. C. Adherent PMNs at 6 h post-SE and Th1 cells at 24 h post SE are shown in cerebral vessels (arrows). Scale bar: 100 µm. D-G. Cells were pretreated with 100 µg/ml PS/2 mAb for 15 min at 25° C. Control cells received no treatment, and were differentially labeled to allow analysis of control and antibody-treated cell in the same venule. The behavior of >150 cells in 3 venules were analyzed. In other experiments untreated cells were injected and their behavior analyzed, and then 100 µg anti-VCAM-1 or anti-MAdCAM-1 mAbs were injected to assess the effects of vascular adhesion molecule blockade on behavior. 5 venules were analyzed for each treatment 6 h post-SE. Hemodynamic parameters were not affected. Bars depict rolling and arrest fractions (mean±SEM) as percentage of control cells (untreated for anti-α4 comparison; behavior prior to antibody injection for anti-VCAM or MAdCAM) that rolled and arrested in the same venule. Groups were compared with control using Kruskall-Wallis test followed by Bonferoni correction of P. **P<0.01; *P<0.001.

Figure 4:
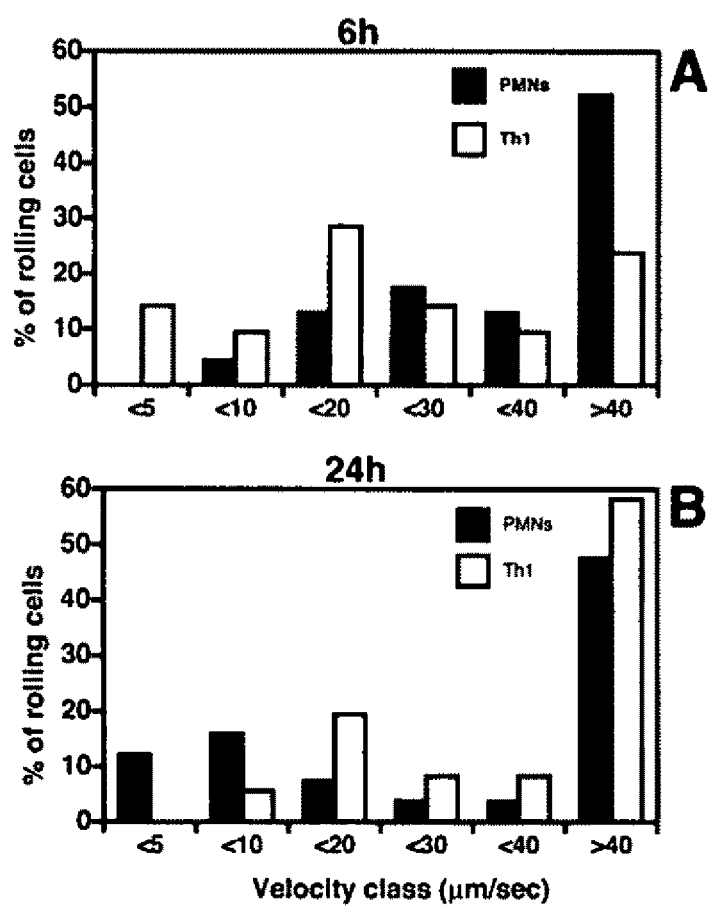

FIG. 4A.B. Frequency distribution of Vroll at 6 h and 24 h post-SE. A. B. Frequency distributions of Vroll were calculated after cells were assigned to velocity classes from >0 µm/s to 5 µm/s; 5 to 10 µm/s; 10 to 20 µm/s; and so on. Neutrophils displayed a similar median rolling velocity (Vroll) at 6 h and 24 h after SE, suggesting that similar mechanisms might account for rolling interactions at the two time points (A, B). (see also Tables 3 and 4). The median Vroll for Th1 lymphocytes was 18 µm/s at 6 h versus 46 µm/s at 24 h post-SE (Tables 3 and 4), while the distribution in velocity classes showed a larger number of cells with higher Vroll at 6 h. The transition differences in rolling velocity in conjunction with the doubling of the rolling fraction is consistent with the expression of additional vascular adhesion mechanisms in the acute and subacute phases of seizure-induced inflammation.

FIG. 5A-E. Blockade of alpha4 integrin inhibits seizures and epilepsy. (A-D) 12 animals/group were monitored for 6 h/day for 30 consecutive days post SE. One representative experiment from a series of 4 with similar results is shown. (A) Daily frequency of convulsions per group was monitored post SE. Epileptic group received treatment with vehicle (PBS). (B) Change in weight (Δweight from the baseline at day 0, prior to SE induction) is shown. (C, D) The average number of convulsions/day and the total number of convulsions were calculated for each group. (***P<0.001; *P<0.0001). To study the therapeutic effect, mice were treated with 200 µg anti-α4 integrin mAb i.p. 1 h after SE onset and then received 200 µg anti-α4 mAb every other day for 20 days. To study the preventive effect, mice were treated with 200 µg anti-α4 integrin mAb i.p. 2 h before injection of pilocarpine and then received 200 µg anti-α4 mAb every other day for 20 days. (E) Cognitive evaluation based on enriched open field exploration (in red the animal tracks during the 10 minutes test) is shown in 3 representative animals per group.

FIG. 6A-E. Telemetry EEG analysis of anti-α4 integrin treated mice. EEG and movements for each animal were acquired 24 h/day for 20 consecutive days. Given the continuum of data (24 h/day) we have evaluated the effect of the treatment as average per total period of recording. Cluster of ictal spikes >3sec were considered as seizures. The minimal interictal interval between 2 different clusters of spikes was 3 sec. Representative EEG tracks starting 1 h after SE are shown for the epileptic group (A) treated with vehicle, anti-α4-pretreated (B) and therapeutic treatment starting 1 h after SE (C). Tracks from baseline, SE and chronic phase are provided. The average number of seizures (D) and seizure duration (E) were calculated in 3 animals/group (One-way ANOVA ***, P<0.0001).

FIG. 7A-C. Control mAb has no effect on the induction of seizures and epilepsy. 10 animals/group were monitored for 6 h/day for 30 consecutive days post SE. The average number of convulsions/day and the total number of convulsions were calculated for each group. Mice were treated with 200 µg anti-CD45 mAb (30G12) i.p. 2 h before injection of pilocarpine and then received 200 µg mAb every other day for 20 days (A and B). (C) Cognitive evaluation based on enriched open field exploration (in red the animal tracks during the 10 minutes test) is shown in 3 representative animals per group.

Figure 8:
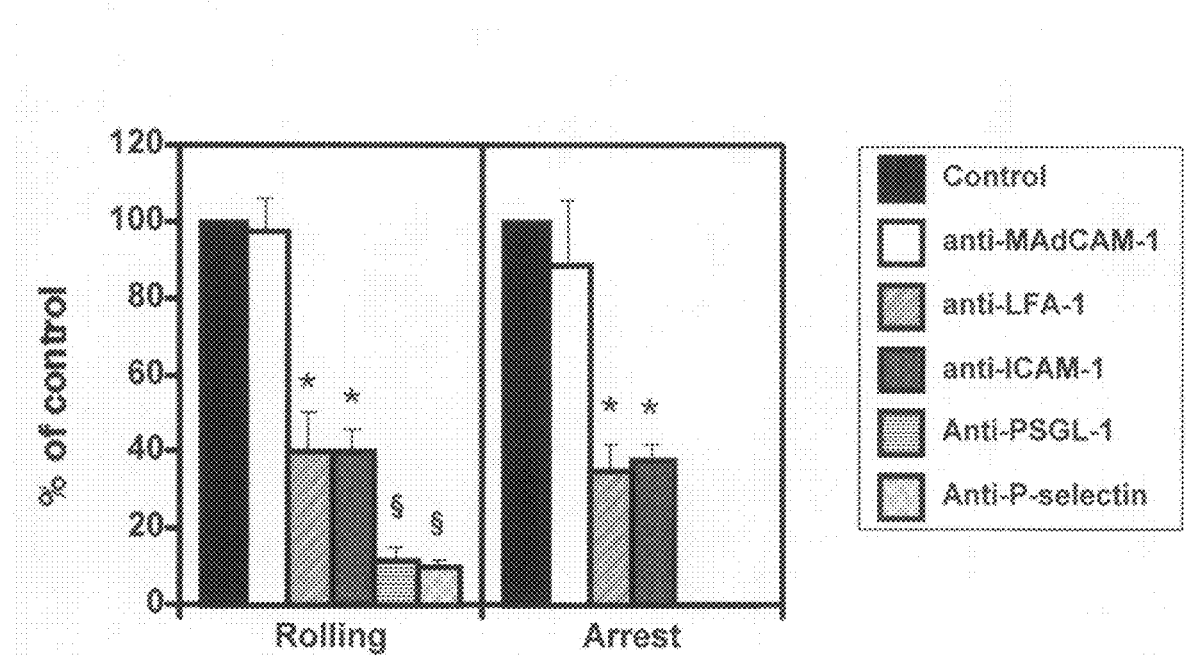

FIG. 8. LFA-1/ICAM-1 and PSGL-1/P-selectin inhibition blocks adhesive interactions in inflamed brain venules after seizures. The behavior of PMNs was studied at 6 h post-SE. Cells were CMFDA-labeled or CMTMR-labeled. Between 4-6 venules/experimental condition were analyzed. Mean±SEM are shown. Cells were pretreated with 100 µg/ml blocking mAb for 15 min at 25° C. Control cells received no treatment, and were differentially labeled to allow analysis of control and antibody-treated cell in the same venule. The behavior of >150 cells/venule were analyzed. In other experiments untreated cells were injected and their behavior analyzed, and then 100 µg anti-ICAM-1, anti-MAdCAM-1 or anti-P-selectin mAbs were injected to assess the effects of vascular adhesion molecule blockade on behavior. Hemodynamic parameters were not affected. Bars depict rolling and arrest fractions (mean±SEM) as percentage of control cells (untreated for anti-LFA-1/PSGL-1 comparison; behavior prior to antibody injection for anti-ICAM, anti-MAdCAM-1 or P-selectin) that rolled and arrested in the same venule. Groups were compared with control using Kruskall-Wallis test followed by Bonferoni correction of P. *P<0.01; §P<0.001.

FIG. 9A-C. Effect of anti-LFA-1 and anti-ICAM-1 therapy on pilocarpine-induced epilepsy. 10 animals/group were monitored for 6 h/day for 30 consecutive days post SE. One representative experiment from a series of 2 with similar results is shown. (A, B) Daily frequency of convulsions per group was monitored post SE. Epileptic group received treatment with vehicle (PBS). The average number of convulsions/day and the total number of convulsions were calculated for each group. To study the therapeutic effect, mice were treated with 200 µg anti-αL integrin or anti-ICAM-1 mAb i.p. 30 min after SE onset and then received 200 µg mAb every other day for 20 days. To study the preventive effect, mice were treated with 200 µg anti-αL integrin or anti-ICAM-1 mAb i.p. 2 h before injection of pilocarpine and then received 200 µg mAb every other day for 20 days. *P<0.0001. (C) Cognitive evaluation based on enriched open field exploration (in red the animal tracks during the 10 minutes test) is shown in 3 representative animals per group.

Figure 10:
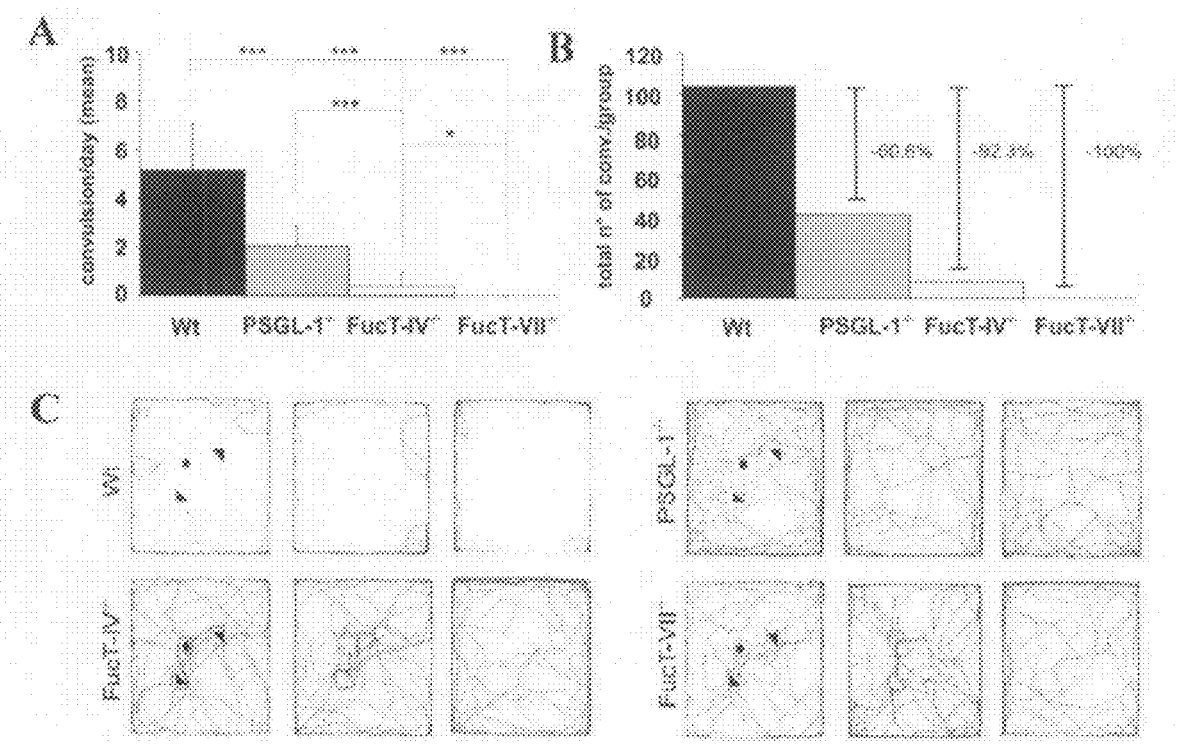

FIG. 10A-C. Effect of PSGL-1 and FucTs deficiency on the induction of epilepsy. 10 animals/group (A and B) were monitored for 6 h/day for 30 consecutive days post SE. One representative experiment from a series of 3 with similar results is shown. The average number of convulsions/day and the total number of convulsions were calculated for each group. (***P<0.001; *P<0.0001). (C) Cognitive evaluation based on enriched open field exploration (in red the animal tracks during the 10 minutes test) is shown in 3 representative animals per group.

Figure 11:
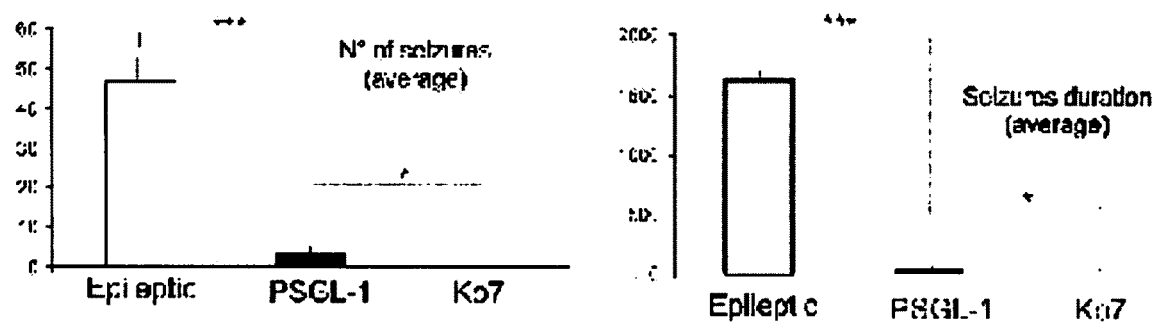

FIG. 11. Telemetry EEG analysis of PSGL-1 and FucT-VII deficient mice. EEG and movements for each animal were acquired 24 h/day for 20 consecutive days. Given the continuum of data (24 h/day) we have evaluated the effect of the treatment as average per total period of recording. Cluster of ictal spikes ≧3sec were considered as seizures. The minimal interictal interval between 2 different clusters of spikes was 3 sec. The average number of seizures and seizure duration were calculated in 3 animals/group (One-way ANOVA *, P<0.0001; ***P<0.001).

Figure 12:
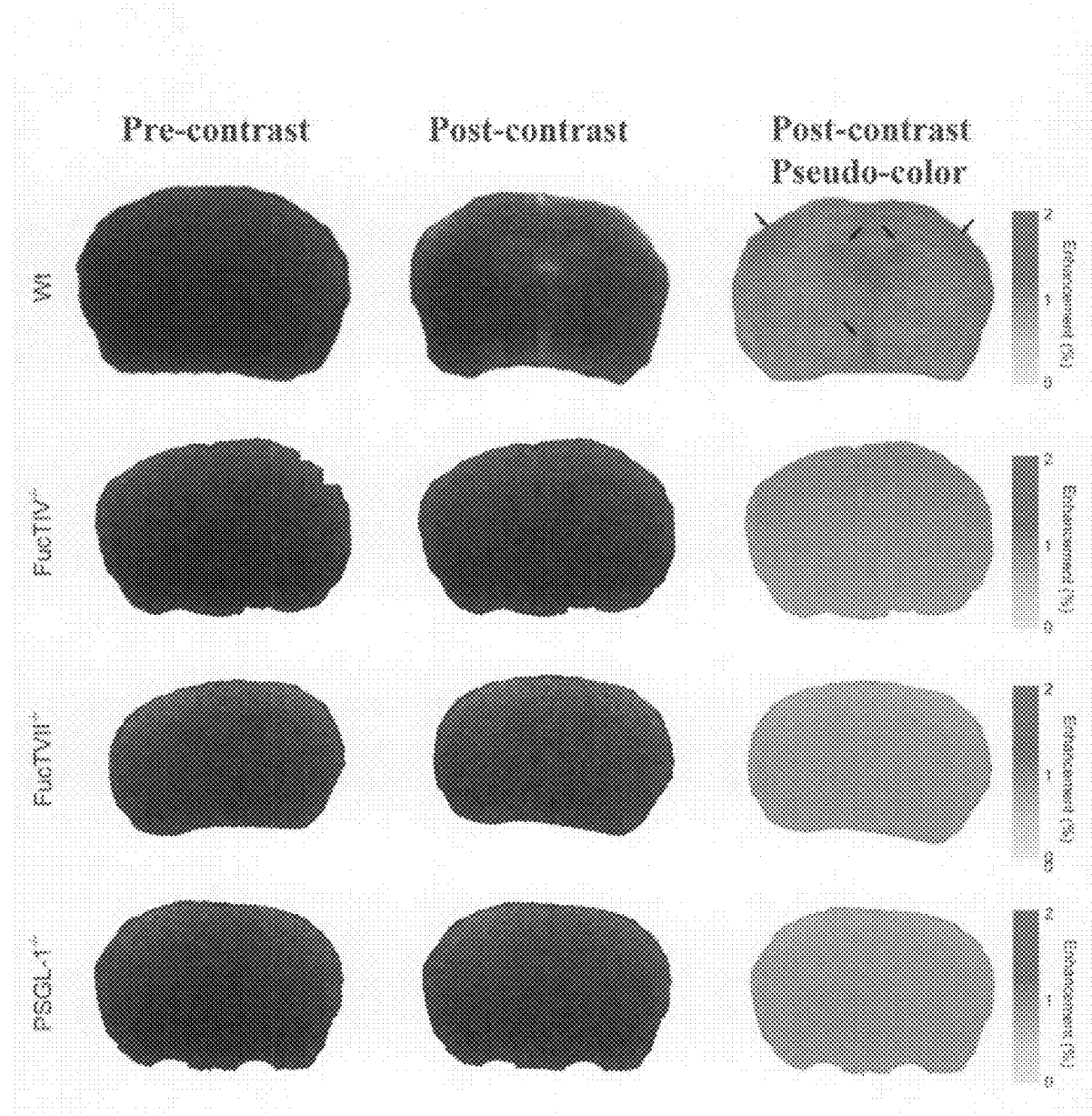

FIG. 12. Evaluation of vascular alterations post-SE in wt and PSGL-1 and FucTs deficient mice. The blood-brain barrier permeability was studied by the mean of intravenously administered Magnevist® (Nmethylglucamine salt of gadolinium complex of diethylenetriamine pentaacetic acid) a paramagnetic iron oxide contrast agent in MRI. Pre-contrast image of an animal after SE, Post-contrast image of the same mouse and pseudo-color map evidencing contrast agent spreading in the cortical areas (arrows) nearby the middle cerebral artery are provided. Extravasated blood from parenchyma is drained by choroid plexus in the cerebral ventricles, which become hyperintense in MRI.

Figure 13:
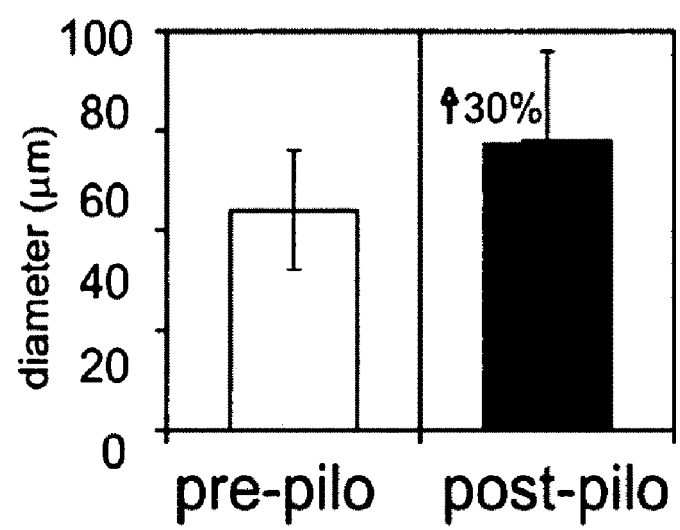

FIG. 13. Increased vascular diameter after Status epilepticus. Blood vessels diameter was measured before and after pilocarpine administration (6 h) as described for intravital microscopy experiments.

Figure 14:
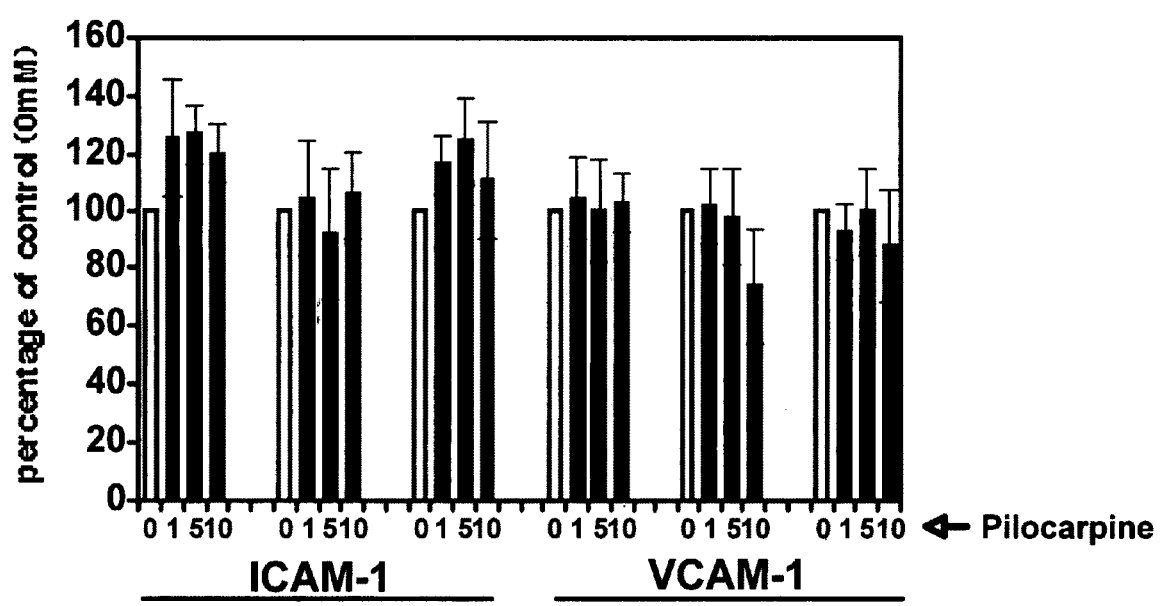

FIG. 14. Effect of pilocarpine on leukocyte adhesion. Total leukocytes were isolated from the blood of normal mice by using hypotonic lysis of erythrocytes. Adhesion assays were performed on eighteen well glass slides coated with VCAM-1. Cells were treated with pilocarpine at different concentrations and time points as indicated. After 20 min, slides were washed, fixed and computer-assisted enumeration of bound cells was performed. The results are presented as percentage of control (untreated) cells and show no effect of pilocarpine on leukocyte adhesion.

Figure 15:
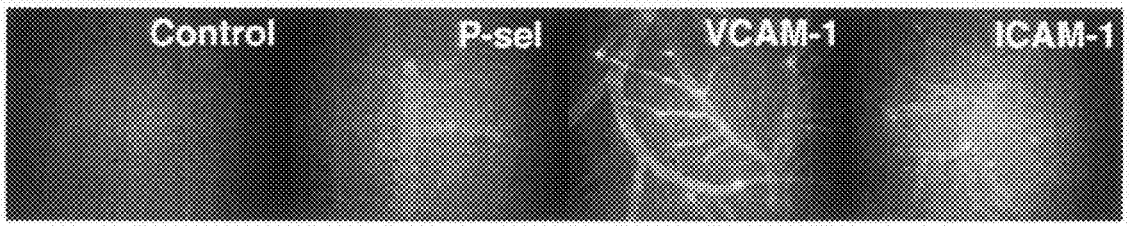

FIG. 15. Induction of adhesion molecules in brain vessels after seizures induced with Kainic acid. Expression of adhesion molecules in cerebral vessels was determined 24 h after the onset of SE in mice receiving i.p. 30 mg/kg Kainic acid (Cayman Chemicals, Mich., USA). Mice received 50 µg of Alexa488-labeled mAb intravenously. An isotype-matched antibody was used as control. In vivo staining revealed expression of P-selectin and ICAM-1 and high level expression of VCAM-1 on both venules and arterioles. Control brains reveal low ICAM-1 expression but absence of detectable VCAM-1, E-selectin and P-selectin.

DETAILED DESCRIPTION OF THE INVENTION

Methods are provided for protecting or treating an individual suffering from adverse effects of repeated seizures. Administration of agents that inhibit leukocyte recruitment in the central nervous system are useful in the treatment of seizures, including the prevention of recurrent seizures, and the development of epilepsy.

Therapeutic agents for use in the methods of the invention block adhesion molecules present on endothelial cells or those that are present on leukocytes, including, without limitation, integrin specific antibodies and derivatives thereof, including antibodies and derivatives thereof having specificity for integrins, selectins or mucins; and soluble counter-receptors of selecting, integrins or mucins, e.g. PSGL-1 and fusion proteins derived therefrom, MAC-1 and fusion proteins derived therefrom; and the like. Such fusion proteins may be a fusion between immunoglobulin constant region domains and the soluble form of the counterreceptor.

Repeated seizures can lead by unknown mechanisms to chronic epilepsy, requiring life long anti-convulsant therapy. It is shown herein that leukocyte recruitment plays a key role in the pathogenesis of epilepsy. Repeated seizures induce increased permeability, vasodilatation and expression of VCAM-1 on central nervous system vessels, and migration of leukocytes into the brain. Leukocytes, including granulocytes and T cells, then accumulate in the brains of patients with epilepsy.

Therapeutic treatment with an agent that inhibits leukocyte recruitment inhibits leukocyte interactions with brain vessels, and leads to a drastic reduction in seizure activity. Strikingly, preventive administration blocks recurrent seizures and development of epilepsy. The results provided herein demonstrate an unexpected role for leukocyte recruitment in the pathogenesis of epilepsy, and show that anti-leukocyte adhesion therapy has therapeutic and preventative effects in epilepsy. Molecules demonstrated to have a role in the pathogenesis of epilepsy include VLA-4, VCAM-1, LFA-1, ICAM-1 and PSGL-1.

Leukocyte recruitment into tissues through the vascular endothelium typically involves a complex interaction between endothelial cells (EC) present in vessel walls, e.g. high endothelial venules; activating agents, such as cytokines and chemokines; and leukocyte recruitment and migration. A progressive sequence of binding events among cognate pairs of EC CAMs and leukocyte ligands serves as a prelude to leukocyte transmigration across endothelium. These steps are usually described as tethering, rolling, leukocyte activation, and firm adhesion. Generally recruitment involves interaction between proteins present on endothelial cells, e.g. selectins, ICAM, VCAM, etc., and proteins present on leukocytes, e.g. integrins, L-selectin, mucin PSGL-1, etc. Humanized anti-adhesion molecule antibodies; and soluble counterreceptors and fusion products derived therefrom are publicly available and their toxicity, beneficial and undesired effects have been studied in several human inflammatory diseases.

Recruitment may also involve chemokines and chemokine receptors. In some embodiments of the invention blockade of chemokine signaling involved in leukocyte trafficking to the central nervous system is used as a therapeutic option.

Adhesion Molecules

In some embodiments of the invention, the therapeutic agent is an integrin antagonist, for example an antagonist, including monoclonal antibodies having specificity for an integrin, e.g. a β2 integrin, a β1 integrin, a β7 integrin, an αI, αM, αX, αD, α4, α9, αv, etc. In one embodiment of the invention, the agent is an antagonist of α4 integrin, an antagonist of CD11b, an antagonist of CD11a, or an antagonist of CD18.

The integrin family includes a number of molecules involved in leukocyte trafficking and recruitment. On leukocytes, the β2-integrin subunit (CD18) forms various heterodimers with α-integrin subunits, e.g. αLβ2 (LFA-1), αMβ2, αXβB2, αDβ2, enabling their interactions with counter receptors of the IgG-domain family on the surface of activated endothelial cells or multiple ligands of the extracellular matrix. These diverse interactions allow firm adhesion of chemokine-stimulated leukocytes to endothelial cells, followed by diapedesis and chemotaxis through damaged or infected tissues. Reagents include antibodies or antibody fragments, e.g. see U.S. Pat. Nos. 6,689,869; 5.997,687, herein incorporated by reference.

The αMβ2 integrin is of particular interest. It is expressed in monocytes, granulocytes, macrophages and natural killer cells and has been implicated in diverse responses of these cells, including phagocytosis, cell-mediated killing and chemotaxis. These complex responses depend on the capacity of αMβ2 integrin to mediate leukocyte adhesion and migration, playing a central role in inflammation. αMβ2 and also αXβ2 integrins recognize a large set of structurally unrelated ligands, including fibrinogen, complement fragment iC3b, ICAM-1, Factor X, JAM's and denatured proteins. Reagents specific for αMβ2 include humanized antibodies and antibody fragments specific for alphaM (CD11b) and for beta2 as described above.

Also of particular interest is αLβ2 integrin (LFA-1). For example the antibody RAPTIVA binds to the αL subunit (CD11a). RAPTIVA inhibits the binding of LFA-1 to intercellular adhesion molecule-1 (ICAM-1), thereby inhibiting the adhesion of leukocytes to other cell types. Interaction between LFA-1 and ICAM-1 contributes to the initiation and maintenance of multiple processes, including activation of T lymphocytes, adhesion of T lymphocytes to endothelial cells, and migration of T lymphocytes to sites of inflammation including psoriatic skin.

αDβ2 integrin is expressed on eosinophils, monocyte/macrophages and neutrophils and is an alternative receptor for VCAM-1.

α4β1 and α9β1 are dual specific integrins that recognize fibronectin at sites distinct from the major RGD containing cell binding site, and VCAM-1 exposed on endothelial cells. The α4β1 and α9β1 integrins appear to specifically enhance cell migration. During inflammation, leukocyte migration across the endothelium is facilitated by the interaction of α4β1 with VCAM-1. Integrin α4β1 induced cell migration depends on the interaction of the α4 cytoplasmic tail with the focal adhesion adaptor protein paxillin. α9β1 integrin also interacts with paxillin, but it lacks the regulatory phosphorylation site and enhances cell motility independent of paxillin binding. αvβ1 integrin has specificity for RGD containing extracellular ligands.

The αv subunit can bind several different β-integrin subunits (αvβ1, αvβ3, αvβ5, αvβ6, αvβ8) forming heterodimers with specificities for RGD peptide containing ligands. Among these different heterodimers, αvβ3 integrin is the most studied in association with cell migration.

The β7-integrin subunit, like β2-integrin, is expressed exclusively in cells of the hematopoietic system. The β7-integrin subunit pairs with the α4 and αE integrin chains forming α4β7 and αEβ7 integrins. α4β7 is involved in the morphogenesis of the gut-associated lymphatic system, while αEβ7 regulates immuno-surveillance of the skin. The β7-integrins are also involved in CD8$^+$ T-cell mediated graft rejection.

One of the endothelial molecules involved in lymphocyte trafficking is vascular adhesion protein-1 (VAP-1). VAP-1 is a cell-surface enzyme belonging to a specific group of amine oxidases (semicarbazide-sensitive amine oxidases [SSAOs] Enzyme Commission 1.4.3.6) that catalyze oxidative deamination of primary amines (see, for example, Salmi et al. (1992) Science 257:1407-1409; Koskinen et al. (2004) Blood 103:3388-3395). VAP-1 mediates PMN-endothelial cell interactions in vitro and in vivo. The adhesive function of VAP-1 is dependent on its enzymatic activity during the rolling and transmigration steps of the extravasation cascade under physiologically relevant shear conditions. Blocking the SSAO activity by enzyme inhibitors, e.g. by BTT-2027, effectively ameliorates the development of an inflammatory reaction in vivo, alternatively it has been shown that an anti-VAP-1 mAb blocks extravasation of PMNs.

The selectins and the immunoglobulin (Ig) superfamily are 2 different families of apical surface EC adhesion molecules responsible for leukocyte recruitment from blood. Selectins are adhesion molecules involved in tethering and rolling of lymphocytes during the migration into lymphoid or non-lymphoid organs. Three selectins have been identified: L-, P- and E-selectin. All three selectins are type I transmembrane glycoproteins that bind sialylated carbohydrate structures in a Ca2+-dependent manner. Each selectin has a lectin-like domain and various numbers of consensus repeat domains which show homology to complement regulatory proteins. The lectin domains of the three selectins share about 60% homology, which results in subtle differences in carbohydrate binding and confers selectin specificity.

L-selectin (CD62L) is expressed on the microvillae of naïve lymphocytes and central memory T cells and is important for lymphocyte homing and adhesion to high endothelial cells of post capillary venules of peripheral lymph nodes and Peyer's patches. L-selectin is critical to the capture/tethering during the migration through the endothelial lining. It interacts with endothelial mucin MAdCAM-1 in Peyer's patches. In addition, L-selectin binds to endothelial ligands, most of which are characterized by MECA-79 reactivity and are collectively known as peripheral node addressins (PNADs). The glycoprotein structure(s) that express the MECA-79 antigen are not completely known, but include CD34. It has been also reported that L-selectin might interact with mucin PSGL-1 (P-selectin glycoprotein ligand-1) expressed by adhered leukocytes and this may help to deliver L-selectin bearing lymphocytes in sites of inflammation.

P-selectin (CD62P) is costitutively expressed on the endothelium of lung and choroids plexus microvessels and on the platelet surface after activation, while E-selectin is constitutively expressed in normal skin vessels. Both E- and P-selectin are upregulated by inflamed endothelium in most organs during inflammatory diseases. PSGL-1 is considered the main lymphocyte ligand for P-selectin and is also able to bind E- and L-selectin. Although PSGL-1 mucin is expressed by all T cells, it is not always glycosylated properly for selectin binding and this explains why naïve T cells cannot bind P- and E-selectins.

All selectin ligands are carbohydrate-containing molecules, and several glycosyltransferases have a role in the biosynthesis of selectin ligands. These include two α1,3-fucosyltransferases, FucT-IV and FucT-VII, the O-linked branching enzyme core 2 β1,6-glucosaminyltransferase-I (C2GlcNAcT-I), a β1,4-galactosyltransferase-I(b1,4GalT-I), and at least two sialyltransferases of the ST3Gal family that add sialic acid to galactose in a 2-3 linkage. In addition, at least one of two tyrosine sulphotransferases must be active to produce high-affinity P-selectin binding, and the sulphated tyrosine residues of PSGL-1 directly participate in P-selectin binding.

P-selectin glycoprotein ligand-1 (PSGL-1) is a dimeric, mucin-type glycoprotein ligand originally identified as a ligand for P-selectin. PSGL-1 is expressed on the surface of all lymphocytes and is a ligand for E- P- and L-selectin. Much attention has been given to the N-terminal region of PSGL-1 as it contains binding regions for the selectins. P-selectin binds to the extreme N terminus of PSGL-1 by interacting stereo specifically with clustered tyrosine sulfates and a nearby core 2O-glycan with a sialyl Lewis x (sLex) epitope (C2-O-sLex). Similarly, L-selectin binds with high affinity to the N-terminal region of PSGL-1 through cooperative interactions with three sulfated tyrosine residues and an appropriately positioned C2-O-sLex O-glycan. E-selectin-PSGL-1 binding seems to be sulfation-independent requiring sLex and glycosylation of PSGL-1 by alpha (1,3) fucosyltransferases. Expression of Cutaneous lymphocyte antigen (CLA,) a fucosyltransferaseVII-dependent carbohydrate modification of PSGL-1, is closely correlated with interactions between PSGL-1 and E-selectin. It has been previously demonstrated that FucT-VII expression is high in Th1 cells, while Th2 lymphocytes expresses high levels of FucT-IV, but not FucT-VII. Moreover, Th1 cells, but not Th2 cells, are able to bind to P-selectin and E-selectin. It has been shown that targeted deletions of the FucT-IV and FucT-VII loci yield a severe attenuation of lymphocyte migration to secondary lymphoid organs and to sites of cutaneous inflammation. Moreover, it has been recently shown that efficient recruitment of activated lymphocytes to the brain in the contexts mimicking EAE is controlled by FucT-VII and its cognate cell surface antigen CLA expressed by PSGL-1.

PSGL-1-mediated tethering and rolling in vivo depends on the interactions with E and P-selectin expressed by endothelium or by P-selectin presented by adhered platelets on the vessel wall. Moreover, it has been shown that also the interactions between the leukocyte adhesion receptor L-selectin and PSGL-1 play an important role in vivo in regulating the inflammatory response by mediating leukocyte tethering and rolling on adherent leukocytes.

An agent of interest is YSPSL, also referred to as (rPSGL-Ig). YSPSL is a recombinant molecule resulting from fusion of P-selectin glycoprotein ligand (PSGL-1) and human IgG1, and is described, inter alia, by Opal et al. (2001) Shock 15:285,290; and Scalia et al. (1999) Circ. Res. 84:93-102, each herein incorporated by reference.

ICAM-1 (CD54) is a type I integral membrane glycoprotein with repeating Ig domains in the extracellular region, a structural signature of the Ig superfamily. Heterogeneity among different cell types gives rise to $M_r$ for ICAM-1 of 97 to 114 kd, most likely resulting from differential patterns of glycosylation. The non-N-glycosylated form has an $M_r$ of 55,000. A second ICAM isoform, ICAM-2 (CD102; $M_r$ 55-65 kd), is partially homologous to ICAM-1 but has only 2 Ig-like extracellular domains compared with 5 such domains for ICAM-1. ICAM-1 is believed important for leukocyte recruitment during a wide range of inflammatory and noninflammatory circumstances.

VCAM (CD106, $M_r$ 100-110 kd) is expressed by activated ECs and follicular dendritic cells. The VCAM extracellular domain contains repeating Ig domains, but because of alternate posttranscriptional splicing there are 2 VCAM messenger RNAs, a more abundant full length transcript and a variant that lacks exon 5. The VCAM variant maintains the same cytoplasmic domain but has a shorter extracellular domain. As with E-selectin, the cytoplasmic tail of human VCAM shows substantial homology across species.

ICAM-1, ICAM -2, and VCAM each promote firm adhesion to ECs. Moreover, VCAM and to a greater extent ICAM-1 probably assist leukocyte entry into the interendothelial junction. These Ig-CAMs interact with different integrin heterodimers expressed on the leukocyte surface: ICAM-1 and ICAM-2 interact with leukocyte function-associated antigen-1 (LFA-1) expressed on all leukocytes, ICAM-1 (but not ICAM-2) interacts with macrophage receptor-1 (Mac-1) expressed on neutrophils, and VCAM interacts with very late antigen-4 (VLA-4) on lymphocytes, monocytes, and eosinophils, but only rarely expressed on neutrophils.

The ability of T cells to leave the circulation depends on their activation state. Activation occurs during rolling, when leukocytes encounter chemoattractants, e.g. C5a, platelet activating factor, leukotriene $B_4$, formyl peptides, and chemoattractant cytokines, e.g. chemokines. Chemokines bind to specific leukocyte receptors that trigger heterotrimeric G-protein-dependent leukocyte signaling. Such signals lead to clustering, and greater affinity/avidity of the integrins LFA-1, Mac-1, and VLA-4 for their cognate Ig-superfamily EC-CAMs. Other intracellular events signaling activation are induced in leukocytes during E-selectin tethering, VLA-4 cross-linking, or LFA-1 binding to ICAM-1. In some embodiments, recruitment of leukocytes is blocked by the administration of agents that inhibit the activity of chemokines or chemokine receptors.

The class of IgCAMS is of interest. These molecules can be involved in the adhesion of leukocytes, e.g. via LFA/ICAM-1, VLA4NCAM-1, etc. The molecules include the following:

| SYSTEMIC IgCAMS | | |
|---|---|---|
| Molecule | Ligands | Distribution |
| ALCAM (CD166) | CD6; CD166; NgCAM; 35 kD protein | Neural; Leukocytes |
| Basigin (CD147) | | Leukocytes; RBCs; Platelets; Endothelial cells |
| BL-CAM (CD22) | Sialylated glycoproteins LCA (CD45) | B-Lymphocytes |
| CD44 | Hyaluronin; Ankyrin; Fibronectin; MIP1β Osteopontin | Lymphocytes; Epithelial; WM perivascular astrocytes |
| ICAM-1 (CD54) | αLβ2; LFA-1 | Leukocytes; Endothelial cells; Dendritic cells; Fibroblasts; Epithelium; Synovial cells |

-continued

SYSTEMIC IgCAMS

| Molecule | Ligands | Distribution |
|---|---|---|
| ICAM-2 (CD102) | αLβ2 (LFA-1) | Endothelial cells; Lymphocytes; Monocytes |
| ICAM-3 (CD50) | αLβ2 | Leukocytes |
| Lymphocyte function antigen-2 (LFA-2) (CD2) | LFA-3 | Lymphocytes; Thymocytes |
| LFA-3 (CD 58) | LFA-2 | Leukocytes; Stroma Endothelial cells Astrocytoma |
| MAdCAM-1 | α4β7; L-selectin | Mucosal endothelial cells |
| PECAM (CD31) | CD31; αvβ3 | Leukocytes; Synovial cells Endothelial cells |
| VCAM-1 | α4β1; α4β7 | Satellite cells Monocytes; Synovial cells; Activated endothelial cells |

In addition to adhesion molecules, leukocyte migration and/or trafficking may be inhibited with agents that act to inhibit chemokines or chemokine receptors. Chemokine/chemokine receptor pairs relevant to leukocyte migration and trafficking include, for example, CCL2(MCP-1)/CCR2; CCL3 (MIP1alpha)/CCR1, CCR5; CCL4(MIP-1beta)/CCR5; CCL5 (RANTES)/CCR5; CCL17 (TARC)/CCR4; CCL22 (MDC)/CCR4; CCL19 (MIP-3beta)/CCR7; CCL21 (SLC)/CCR7; CXCL1(Gro-alpha)/CXCR2; CXCL8 (IL8)/CXCR1, CXCR2; CXCL9 (MIG)/CXCR3; CXCL10 (IP-10)/CXCR3; and CXCL12 (SDF-1)/CXCR4; and CCR1 and its ligands. In addition to chemokines, agents that inhibit other chemoattractants or chemoattractant receptors can inhibit leukocyte migration and/or trafficking. Chemoattractant /receptor pairs relevant to leukocyte migration and trafficking include LTB4/BLT1, complement component C5a/C5aR, and chemerin/CMKLR1. Agents, e.g. small molecule antagonists, monoclonal antibodies, etc. that interfere with the interaction between a chemokine or other chemoattractant with its cognate receptor are useful in the methods of the invention.

Alternatively, blocking integrin-outside in signaling may be used to inhibit leukocyte trafficking to the central nervous system. Blockade of signal transduction pathways generated after integrin engagement (outside-in signaling) inhibits adhesion stabilization and migration of leukocytes in sites of inflammation. As for instance blockade of interactions between the cytoplasmic tail of alpha4 integrins and paxillin. Paxillin, a signaling adaptor molecule, binds directly to the alpha4 cytoplasmic tail and its binding is important for cell migration. Interfering with alpha4 signaling by inhibiting the alpha4-paxillin interaction decreases alpha4-mediated cell migration and adhesion to VCAM-1 and MadCAM under shear flow. These in vitro effects are accompanied by a selective impairment of leukocyte migration into inflammatory sites when the alpha4-paxillin interaction is blocked in vivo. Similarly, it has been shown that perturbance of outside-in signaling by beta2 integrins impairs the inflammatory responses in animal models (Lowel and Berton, PNAS, 1998; Vicentini et al., J. Immunol., 2002; Evangelista et al., Blood 2007, each specifically incorporated by reference). Thus, drugs that block alpha4beta1-integrin or alphaLbeta2 and alphaMbeta2 integrin outside-in signaling can have therapeutic effects for seizures and epilepsy. These in vitro effects are accompanied by a selective impairment of leukocyte migration into inflammatory sites when the alpha4-paxillin interaction is blocked in vivo (Feral etal., 2006J. Clin. Invest 116, 715-723).

Adhesion Molecule Antagonists

As used herein, an "antagonist," refers to a molecule which, when interacting with (e.g., binding to) a target protein, decreases the amount or the duration of the effect of the biological activity of the target protein (e.g., interaction between leukocyte and endothelial cell in recruitment and trafficking). Antagonists may include proteins, nucleic acids, carbohydrates, antibodies, or any other molecules that decrease the effect of a protein. Unless otherwise specified, the term "antagonist" can be used interchangeably with "inhibitor" or "blocker".

The term "agent" as used herein includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

Antagonists of interest include antibodies specific for one or more adhesion molecules involved in leukocyte recruitment or trafficking to the central nervous system. Also included are soluble receptors, conjugates of receptors and Fc regions, and the like. Generally, as the term is utilized in the specification, "antibody" or "antibody moiety" is intended to include any polypeptide chain-containing molecular structure that has a specific shape which fits to and recognizes an epitope, where one or more non-covalent binding interactions stabilize the complex between the molecular structure and the epitope. The archetypal antibody molecule is the immunoglobulin, and all types of immunoglobulins (IgG, IgM, IgA, IgE, IgD, etc.), from all sources (e.g., human, rodent, rabbit, cow, sheep, pig, dog, other mammal, chicken, turkey, emu, other avians, etc.) are considered to be "antibodies." Antibodies utilized in the present invention may be polyclonal antibodies, although monoclonal antibodies are preferred because they may be reproduced by cell culture or recombinantly, and may be modified to reduce their antigenicity.

Antibody fusion proteins may include one or more constant region domains, e.g. a soluble receptor-immunoglobulin chimera, refers to a chimeric molecule that combines a portion of the soluble adhesion molecule counterreceptor with an immunoglobulin sequence. The immunoglobulin sequence preferably, but not necessarily, is an immunoglobulin constant domain. The immunoglobulin moiety may be obtained from IgG1, IgG2, IgG3 or IgG4 subtypes, IgA, IgE, IgD or IgM, but preferably IgG1 or IgG3.

A straightforward immunoadhesin combines the binding region(s) of the "adhesin" protein with the hinge and Fc regions of an immunoglobulin heavy chain. Ordinarily nucleic acid encoding the soluble adhesion molecule will be fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics.

Antibodies that have a reduced propensity to induce a violent or detrimental immune response in humans (such as anaphylactic shock), and which also exhibit a reduced propensity for priming an immune response which would prevent repeated dosage with the antibody therapeutic are preferred for use in the invention. These antibodies are preferred for all administrative routes, including intrathecal administration. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Alternatively, polyclonal or monoclonal antibodies may be produced from animals which have been genetically altered to produce human immunoglobulins, such as the Abgenix XenoMouse or the Medarex HuMAb® technology. Alternatively, single chain antibodies (Fv, as described below) can be produced from phage libraries containing human variable regions.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment" or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Small molecule agents encompass numerous chemical classes, though typically they are organic molecules, e.g. small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of $GABA_A$ inhibitors can be prepared by syntheses of combinatorial chemical libraries (see generally DeWitt et al, *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

Candidate antagonists can be tested for activity by any suitable standard means. As a first screen, the antibodies may be tested for binding against the adhesion molecule of interest. As a second screen, antibody candidates may be tested for binding to an appropriate cell line, e.g. leukocytes or endothelial cells, or to primary tumor tissue samples. For these screens, the candidate antibody may be labeled for detection (e.g., with fluorescein or another fluorescent moiety, or with an enzyme such as horseradish peroxidase). After selective binding to the target is established, the candidate antibody, or an antibody conjugate produced as described below, may be tested for appropriate activity, including the ability to block leukocyte recruitment to the central nervous system in an in vivo model, such as an appropriate mouse or rat epilepsy model, as described herein.

Currently available therapeutic agents for blocking leukocyte recruitment include polypeptide therapeutics, e.g. antibodies, monoclonal antibodies, receptor-Fc chimeric fusion proteins, etc., and small molecule-based drugs. There are now multiple clinically validated anti-adhesion drugs. Small-molecule antagonists of adhesion molecule function can be categorized into three distinctive modes of action: ligand-mimetic competitive antagonists and allosteric antagonists or a I allosteric antagonists.

Approved therapies comprise an antibody fragment, ReoPro™, and two small-molecule inhibitors, Integrilin™ and Aggrastat™. These structures built on previously published structures of an integrin binding to its RGD based ligand. This information may yield additional routes to drug discovery that target medically relevant integrins.

The LFA-1/ICAM interaction is another key mediator of cell adhesion between leukocytes and vascular endothelium and, as both molecules are expressed on leukocytes, they are involved in modulating immune responses. In particular, targeting the integrin α chain (CD11a) has led to clinical success. The monoclonal antibody efaluzimab (Raptiva™) specifically recognizes the α chain of αLβ2. It inhibits the ability of T cells to interact with Langerhans cells, endothelial cells and keratinocytes. Antisense specifically directed at ICAM-1 (Alicaforsen™) has also been developed and is in clinical trials. Small-molecule approaches have been under active research and has provided a variety of distinct antagonists in pre-clinical studies.

The leukocyte integrin α4β1 interacts with its ligands VCAM and fibronectin. This is a key integrin-ligand interaction that allows leukocytes to adhere strongly to vascular endothelium and trigger subsequent shape changes in the leukocyte, ultimately leading to transmigration. Antibodies and small-molecule antagonists are effective in a wide range of animal models of inflammation. For example SB683699 for multiple sclerosis is being tested for inflammation and has demonstrated positive effects. The anti-VLA4 monoclonal antibody Tysabri/Antegren™ is also in use. Another VLA4 antagonist is CDP323, which is currently in clinical trials. Also in clinical trials is the immunoadhesin molecule YSPS.

Conditions of Interest

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender. The methods of the invention are useful in treating and preventing seizures, particularly recurrent seizures.

There are two kinds of seizure disorders: an isolated, non-recurrent attack, such as may occur during a febrile illness or after head trauma, and epilepsy; a recurrent, paroxysmal disorder of cerebral function characterized by sudden, brief attacks of altered consciousness, motor activity, sensory phenomena, or inappropriate behavior caused by excessive discharge of cerebral neurons. Seizures result from a focal or generalized disturbance of cortical function, which may be due to various cerebral or systemic disorders. Seizures may also occur as a withdrawal symptom after long-term use of alcohol, hypnotics, or tranquilizers. In many disorders, single seizures occur. However, seizures may recur at intervals for years or indefinitely, in which case epilepsy is diagnosed.

Epilepsy is classified etiologically as symptomatic or idiopathic. Symptomatic indicates that a probable cause exists and a specific course of therapy to eliminate that cause may be tried. Idiopathic indicates that no obvious cause can be found. Unexplained genetic factors may underlie idiopathic cases. The risk of developing epilepsy is 1% from birth to age 20 yr and 3% at age 75 yr. Most persons have only one type of seizure; about 30% have two or more types. About 90% have generalized tonic-clonic. seizures. Absence seizures occur in about 25%. Complex partial seizures occur in 18% (alone in 6%; with others in 12%).

Manifestations depend on the type of seizure, which may be classified as partial or generalized. In partial seizures, the excess neuronal discharge is contained within one region of the cerebral cortex. In generalized seizures, the discharge bilaterally and diffusely involves the entire cortex. Sometimes a focal lesion of one part of a hemisphere activates the entire cerebrum bilaterally so rapidly that it produces a generalized tonic-clonic seizure before a focal sign appears.

Simple partial seizures consist of motor, sensory, or psychomotor phenomena without loss of consciousness. The specific phenomenon reflects the affected area of the brain. In complex partial seizures, the patient loses contact with the surroundings for 1 to 2 min. Mental confusion continues another 1 or 2 min after motor components of the attack subside. These seizures may develop at any age. Complex partial seizures most commonly originate in the temporal lobe but may originate in any lobe of the brain. Generalized seizures cause loss of consciousness and motor function from the onset. Such attacks often have a genetic or metabolic cause. They may be primarily generalized (bilateral cerebral cortical involvement at onset) or secondarily generalized (local cortical onset with subsequent bilateral spread). Types of generalized seizures include infantile spasms and absence, tonic-clonic, atonic, and myoclonic seizures.

Absence seizures consist of brief, primarily generalized attacks manifested by a 10- to 30-sec loss of consciousness and eyelid flutterings, with or without loss of axial muscle tone. Affected patients do not fall or convulse; they abruptly stop activity and resume it just as abruptly after the seizure. Generalized tonic-clonic seizures typically begin with an outcry; they continue with loss of consciousness and falling, followed by tonic, then clonic contractions of the muscles of the extremities, trunk, and head. Urinary and fecal incontinence may occur. Seizures usually last 1 to 2 min. Secondarily generalized tonic-clonic seizures begin with a simple partial or complex partial seizure. Atonic seizures are brief, primarily generalized seizures in children. They are characterized by complete loss of muscle tone and consciousness. The child falls or pitches to the ground, so that seizures pose the risk of serious trauma, particularly head injury. Myoclonic seizures are brief, lightning-like jerks of a limb, several limbs, or the trunk. They may be repetitive, leading to a tonic-clonic seizure. There is no loss of consciousness.

Conventional treatment focuses on the use of anticonvulsant drugs. For generalized tonic-clonic seizures, phenytoin, carbamazepine, or valproate is the drug of choice. For partial seizures, treatment begins with carbamazepine, phenytoin, or valproate. If seizures persist despite high doses of these drugs, gabapentin, lamotrigine, or topiramate may be added. For absence seizures, ethosuximide orally is preferred. Valproate and clonazepam orally are effective, but tolerance to clonazepam often develops. Acetazolamide is reserved for refractory cases. Atonic seizures, myoclonic seizures, and infantile spasms are difficult to treat. Valproate is preferred, followed, if unsuccessful, by clonazepam. Ethosuximide is sometimes effective, as is acetazolamide (in dosages as for absence seizures). Phenytoin has limited effectiveness. For infantile spasms, corticosteroids for 8 to 10 wk are often effective.

Carbamazepine may make patients with primary generalized epilepsy and multiple seizure types worse.

Methods

In the broadest sense, methods are provided for inhibiting recurrent seizures, including those associated with epilepsy, in a mammalian host. The host is generally a mammal, e.g. mouse, rat, monkey, etc. and in many embodiments is a human. An inhibitor of leukocyte recruitment or trafficking is administered to a mammalian host, where the administration may follow a seizure, or in the case of a patient with known recurrent disease, may be administered following diagnosis. In addition to seizure activity, the patient may be screened for evidence of CNS inflammation, e.g. by MRI, etc.

The inhibitor of leukocyte recruitment or trafficking may be administered in a single dose, or may be administered at regular intervals, e.g. at least weekly, daily, or every two days, and may be administered twice daily, or more often, e.g. around about every 4-8 hours. Typically, after administration the blocker reaches therapeutic levels in the brain vasculature at least transiently, e.g. for around about 1 minute, at least about 5 minutes, at least about 30 minutes, at least about 1 hour, or more.

Administration of the treatment is maintained for a period of time sufficient to effect a change in CNS leukocyte recruitment or trafficking. Such treatment may involve dosing for at least about one week, at least about two weeks; at least about 3 weeks; at least about one month; at least about two months; at least about four to six months; or longer, for example at least about one or more years. For extended treatment; e.g. treatment of one or more years, a schedule may involve intermittent periods, such as one week on and one week off; two weeks on and two weeks off; one week in a month, etc.

Patients that can benefit from the present invention may be of any age and include adults and children, e.g. young adults. Children, e.g. neonate, infant, early childhood, adolescent, etc. in particular may benefit prophylactic treatment. Children suitable for prophylaxis can be identified by genetic testing for predisposition, e.g. by chromosome typing; by family history, or by other medical means. As is known in the art, dosages may be adjusted for pediatric use. Anti-adhesion therapies may also help prevent the occurrence of epilepsy following brain insults associated with inflammation such as traumatic brain injury, for instance in military personnel in war zones where seizures and epilepsy present a significant health problem.

The inhibitor of leukocyte recruitment or trafficking is generally administered to the host as a pharmaceutical composition that includes an effective amount of the inhibitor of leukocyte recruitment or trafficking in a pharmaceutically acceptable vehicle. In the subject methods, the active agent(s) may be administered to the host using any convenient means capable of resulting in the desired improvement of seizures.

Therapeutic agents can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories,. injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant for example.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

Toxicity and therapeutic efficacy of the active ingredient can be determined according to standard pharmaceutical procedures in cell cultures and/or experimental animals, including, for example, determining the $LD_{50}$ (the dose lethal to 50% of the population, or for the methods of the invention, may alternatively by the kindling dose) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration maybe carried out through the use of an Ommaya reservoir, in accordance with known techniques. (F. Balis et al., Am J. Pediatr. Hematol. Oncol. 11, 74, 76 (1989).

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the mariufacture, use or sale of pharmaceuticals or * biological products, which notice reflects approval by the agency of manufacture, use or sale for human administration.

In another aspect of the invention, candidate agents are screened for the ability to inhibit leukocyte recruitment or trafficking and to prevent seizure recurrence. Such compound screening may be performed using an in vitro model, a genetically altered cell or animal, or purified proteins, particularly the human leukocyte adhesion molecules, or cells expressing such molecules. A wide, variety of assays may be used for this purpose. In one embodiment, compounds that are active in binding assays with the adhesion molecules, or are predicted to be antagonists of the adhesion molecules are then tested in an in vitro culture system. Alternatively, candidate agents are tested for antagonist activity, and may then be assessed in animal models for treatment of seizures.

Compounds that are initially identified by any screening methods can be further tested to validate the apparent activity. The basic format of such methods involves administering a lead compound identified during an initial screen to an animal that serves as a model for humans and then determining the effects on CNS and seizures. The animal models utilized in validation studies generally are mammals. Specific examples of suitable animals include, but are not limited to, primates, mice, and rats.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Experimental and clinical data indicate that the occurrence of repeated seizures can lead to a chronic epileptic condition. In the last decade, vascular alterations and the cytokines, have been discussed in relation to the pathogenesis of epilepsy, suggesting a potential role for inflammatory mechanisms of tissue damage. Leukocyte recruitment is both a hallmark of and a point of potential therapeutic intervention in inflammation, yet white cell recruitment has not been examined after seizures or in epilepsy.

Figure 1:
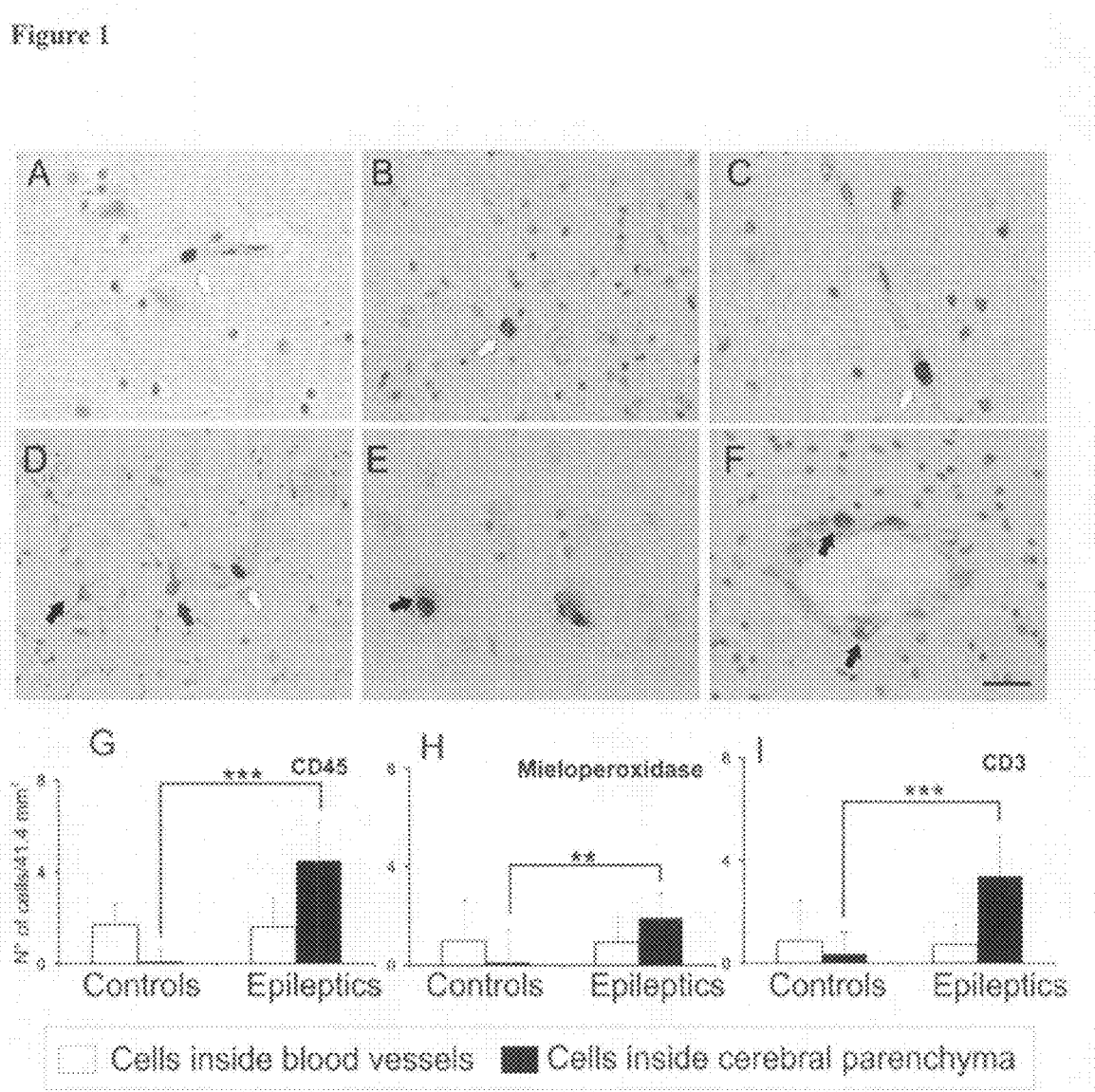
FIG. 1A-I. Leukocyte infiltration in human epileptic brains. Representative brain sections of a patient with non-inflammatory neurological diseases (NIND) (A-C) and of a patient with epilepsy (D-F; see also Table 1). CD45 staining (A,C) revealed leukocytes in brain parenchyma (black arrow), perivascularly (grey arrow) and inside blood vessels (white arrow) (D). Myeloperoxidase staining (B, E) revealed PMNs in brain parenchyma only in the epileptics (E). CD3-positive cells (C, F) were detected only in epilepsy-suffering group of patients (F). All these sections were counter-stained with Nissl staining to outline a precise anatomical evaluation of leukocyte distribution. (G-I) Morphometric analysis was performed to quantify the number of cells±SD/$mm^2$ (5 slides containing 2 brain sections for each human subject were analyzed). We analyzed five regions for each brain section (ROIs; number of cells per 41.4 $mm^2$); regions were selected randomly but had to contain at least one blood vessel. Cells were divided in "inside vessels" and "inside the brain parenchyma". One way-ANOVA statistical evaluation was performed, followed by Bonferroni post-hoc test (*P<0.001; P<0.01). Scale bar is corresponding to 25 µm.

To determine whether human epilepsy is associated with increased leukocyte infiltration in the CNS, we analyzed brain specimens from 10 long-term epileptics with no concurrent inflammatory brain diagnoses, 10 age-matched controls with no neurological diseases and 10 controls with non-inflammatory neurological diseases (NIND) (Table 1A-C). Immunohistologic observations revealed leukocytes in the parenchyma of epileptic brains, but not in control NIND subjects (FIGS. 1D-F and 1A-C respectively). Cells expressing the leukocyte common antigen (CD45) were detectable both in blood vessels and in the brain parenchyma in the epileptic group (FIG. 1D, G), whereas in NIND brains CD45+ cells were confined to the lumena of vessels (FIG. 1A, G). Most of the paranchymal cells were perivascular in location, suggesting recent recruitment. Most importantly, granulocytes and T cells were observed in the brains of all patients with epilepsy. Polymorphonuclear leukocytes (PMNs), identified by myeloperoxidase staining, were much more frequent in the parenchyma in brain specimens of epileptic group (FIG. 1 E, 1H) when compared with control brains (FIG. 1 B, 1H). CD3+ T cells were also more frequent in the parenchyma of epileptic subjects (FIG. 1F and 1I versus control brain, FIG. 1C, 1I). Morphometric analyses are summarized in FIG. 1G-I. Brain sections from patients with no neurological disease were similar to those from NIND patients (N=10). These observations show that leukocytes are recruited to the brain vascular and into the surrounding parenchyma of patients with seizures and suggest an ongoing low level inflammatory process. We hypothesized that leukocyte recruitment might exacerbate the underlying seizure mechanisms.

TABLE 1

Human subjects[1].

| Patient | Gender | Age | Epileptic Condition |
|---|---|---|---|
| A | | | |
| P. D. A. | F | 48 | epileptic |
| P. E. | F | 41 | epileptic |
| C. R. | M | 46 | epileptic in therapy with gardenale |
| M. K. | M | 23 | Generalized epilepsy |
| A. P. K. | M | 33 | epileptic after a traffic crash (2 years ago) |
| M. G. | M | 42 | epileptic in cerebral arteriovenous malformation at the right hemisphere |
| S. S. | M | 50 | epileptic in therapy with drugs |
| P. N. | M | 74 | epileptic in therapy with drugs |
| C. V. | M | 67 | epileptic in therapy with drugs |
| G. G | M | 27 | epileptic in therapy with drugs |
| B | | | |
| O. E. | F | 48 | none |
| B. R. | F | 41 | none |
| B. D. | M | 46 | none |
| M. F. | M | 23 | none |
| C. G. | M | 33 | none |
| V. F. | M | 42 | none |
| B. P. | M | 50 | none |
| B. M. | M | 74 | none |
| V. A. | M | 67 | none |
| P. F. | M | 27 | none |

| C | | | |
|---|---|---|---|
| Patient | Gender | Age | NIND |
| V. G. | M | 89 | Multiinfarctual Demenza |
| D. L. | M | 87 | Parkinson Disease |
| R. T. | F | 76 | Parkinson Disease |
| B. C. | F | 88 | Parkinson Disease |
| P. N. | M | 79 | Parkinson Disease |
| P. M. | M | 77 | Parkinson Disease |
| D. M. | M | 78 | Parkinson Disease |
| G. D. | M | 83 | Parkinson Disease |
| T. I. | F | 65 | Parkinson Disease |
| M. L. | M | 72 | Parkinson Disease |

[1]Cortical samples were obtained from 10 epileptic patients (A), 10 relative age-matched controls (B) and 10 controls with non-inflammatory neurological diseases (NIND) (C). No known cerebral inflammatory diseases were diagnosed as cause of death or before decease. All the brain samples were collected and stored at the Department of Medicine and Public Health, Section of Forensic Medicine, University of Insubria, Varese, Italy.

To test this hypothesis, we turned to a mouse model of epilepsy. Systemic administration of pilocarpine induces limbic seizures in rodents, mimicking temporal lobe epilepsy, the most frequent type of epilepsy in humans. Pilocarpine-induced status epilepticus (SE) is characterized by continuous seizures lasting 1-2 h in our experimental model (in other experimental models, for instance in rats, seizures last up to 24 h), and results in brain injury, leading after a latency phase of 1-2 weeks to establishment of epilepsy characterized by recurrent spontaneous seizures. In addition to hippocampal damage, recent evidence suggests that pilocarpine-induced seizures cause widespread cortical and subcortical lesions.

We looked for vascular modifications as signs of inflammation after SE in mice. In agreement with previous histochemical studies indicative of seizure-induced vascular permeability, contrast agent perfusion followed by MRI revealed focal loss of the of blood brain barrier 6 hours after SE, with a hyperintense signal indicating vascular leakage in the parietal neocortex (FIG. 12 wt). In addition, there was a 30% increase in the diameter of cortical vessels 6 h post SE (FIG. 13). These results are consistent with a condition of acute inflammation affecting brain vessels shortly after seizure activity.

Figure 2:
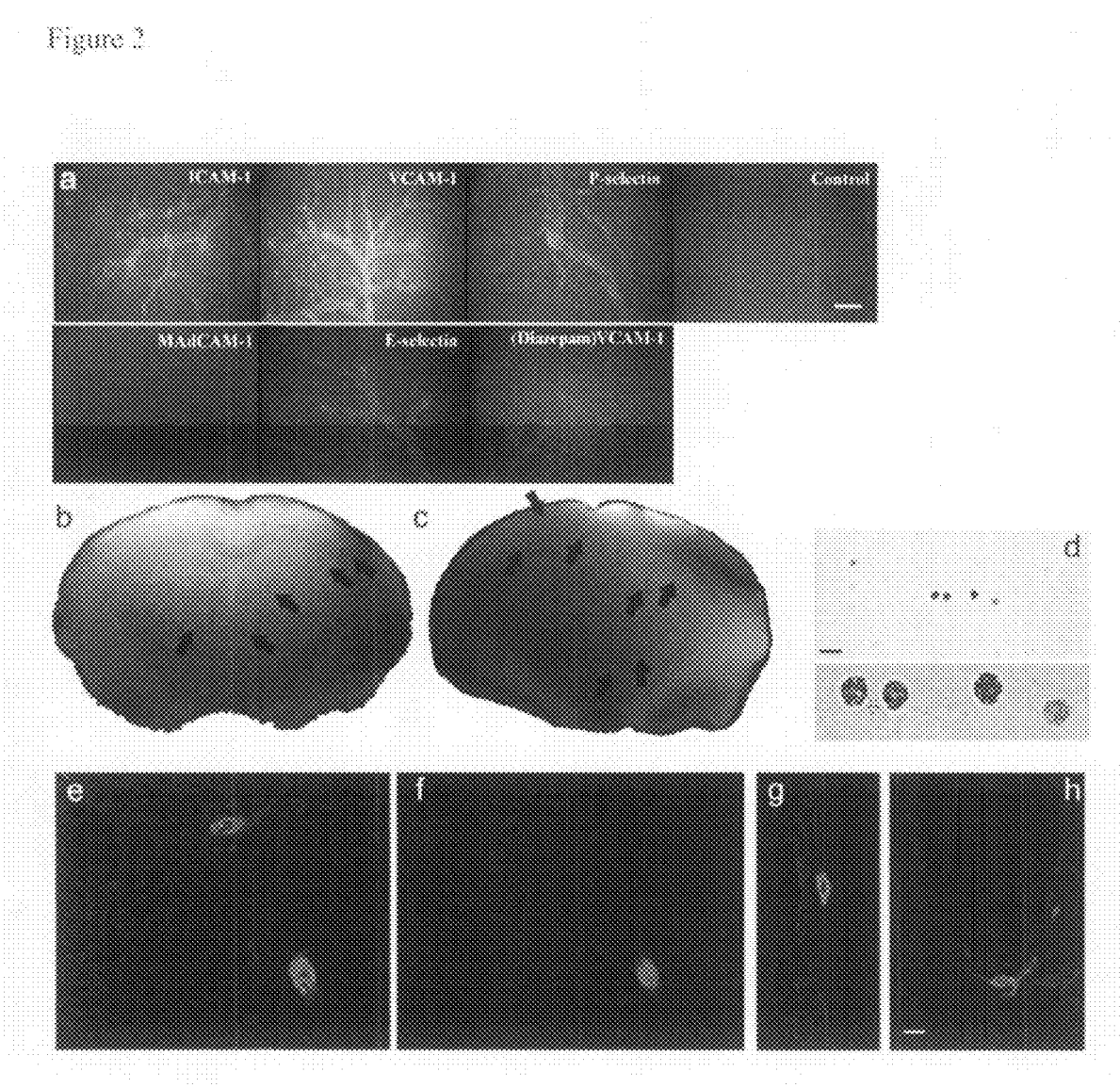
FIG. 2A-H. Induction of vascular adhesion molecules and recruitment of granulocytes and activated lymphocytes into the brain after experimental seizures. (A) Expression of adhesion molecules in cerebral vessels was determined 6 h after the onset of SE. Mice received 50 µg of Alexa488-labeled mAb intravenously. An isotype-matched antibody was used as control. Control brains reveal low ICAM-1 expression but absence of detectable VCAM-1, E-selectin and P-selectin. Brains in which seizure activity was suppressed by administration of 3 mg/Kg Diazepam i.p. 20 min before pilocarpine injection showed an almost undetectable VCAM-1 expression (Diazepam). (B-D) Leukocytes were marked by Resovist® (Schering AG, Germany). This contrast agent consists of superparamagnetic iron oxide (USPIO) nanoparticles coated with carboxydextran. PMNs and Th1 lymphocytes were injected iv into recipients either 2 h (for PMNs) or 24 h (for Th1 cells) after pilocarpine injection. Hypointense MRI spots document intraparenchymal granulocytes (B) and Th1 cells (C) in the brain after SE (24 h after cell transfer). Immuno-histochemical staining with Prussian Blue confirmed the presence of PMNs (D, enlarged in the bottom rectangle) and Th1 cells.

Induction of vascular adhesion molecules involved in leukocyte recruitment is a hallmark of local inflammation. To assess adhesion molecule induction, fluorescence-labeled antibodies to ICAM-1, VCAM-1, P-selectin, E-selectin or MAdCAM-1 were injected iv into mice at various times after pilocarpine-induced SE (FIG. 2 and Table 2). As shown in FIG. 2A, anti-VCAM-1 mAb accumulated at high levels on arteriolar and venular endothelium in the CNS after seizure activity (FIG. 2A, Table 2). ICAM-1 was present at low levels even in control mice, but expression of VCAM-1 was induced following seizure induction, with the highest levels observed at 24 h and 7d post-SE (Table 2). Importantly, pharmacologic suppression of SE by administration of Diazepam prior to pilocarpine injection largely abrogated the upregulation of VCAM-1 (FIG. 2A), suggesting that seizure activity itself contributes to high expression of VCAM-1 in brain vessels. In addition, we observed that anti-P-selectin and anti-E-selectin mAbs accumulated in venular endothelium at 6 h and 24 h after seizures (FIG. 2A and Table 2). Together, these results show that intense seizure activity leads to proinflammatory changes in CNS endothelium, which could support leukocyte recruitment and consequent amplification of inflammatory damage.

TABLE 2

Expression of adhesion molecules post-SE[2]

| | hours/days post induction of seizures | | | |
|---|---|---|---|---|
| | 6 h | 24 h | 7 days | 30 days |
| Control mAb | − | − | − | − |
| MAdCAM-1 | − | − | − | − |
| VCAM-1 | ++ | +++ | +++ | + |
| ICAM-1 | + | + | ++ | + |
| P-selectin | + | ++ | ± | ND |
| E-selectin | + | ++ | + | ND |

[2]Epilepsy was induced in C56Bl/6 mice as described at Materials and Methods section and positivity for adhesion molecules was evaluated at different time points after the induction of SE. Two mice per time-point for each mAb were used. Blinded evaluation showed that cortical brain vessels were positive for VCAM-1, ICAM-1, P-selectin and E-selectin. No positivity was observed with control mAb and anti-MAdCAM-1 mAb (−). ± some venules were positive while other venules were apparently negative; +, low positivity; ++ medium positivity; +++, high positivity; ND, not determined.

We next asked if leukocytes are recruited into the CNS after SE. PMNs and Th1 lymphocytes were labeled with iron particles and tracked by MRI after transfusion iv into recipients either 2 h (for PMNs) or 24 h (for Th1 cells) after pilocarpine injection. 24 h after cell transfer, localization of cells in the neocortex, hippocampus and thalamus was revealed by the appearance of hypointense spots indicating the presence of iron particles (FIG. 2B shows focal neutrophil localization;

2C illustrates Th1 cell localization). No localization of injected cells was detected in the brains of control mice). Histochemical staining of brains after MRI confirmed that the ferric iron particles were associated with labeled cells (FIG. 2D). In independent studies, we injected fluorescence-labeled PMNs 6 h after induction of SE. 24 h later we observed transferred as well as endogenous Gr-1 positive cells in the brain parenchyma. (FIG. 2E, F). Moreover, CD3 staining and confocal microscopy revealed endogenous T cells localized perivascularly 24 h after SE (FIG. 2H). Since pilocarpine does not induce adhesion of leukocytes per se (FIG. 14), the findings suggest that leukocyte recruitment was enhanced as a result of vascular changes induced following SE.

To visualize leukocyte interactions with the brain microvasculature directly, we infused fluorescence labeled PMNs or lymphocytes iv, and monitored their behavior using intravital microscopy. Injected PMNs interacted efficiently, displaying rolling and arrest in brain venules in mice both 6 and 24 h after SE (FIG. 3A-C). The rolling fraction was similar at 6 h and at 24 h, while the fraction of cells that arrested was 2.6 times higher at 6 h, indicating that PMNs are able to stick more efficiently to brain endothelium early after SE. Resting lymphocytes from peripheral lymph nodes did not interact, suggesting that lymphocyte activation might be a prerequisite for the seizure-induced adhesion (FIG. 3A), as it is for lymphocyte-endothelial adhesion in models of experimental allergic encephalomyelitis. Indeed, activated lymphocytes with a Th1 phenotype rolled and stuck efficiently in CNS vessels after seizure activity. Th1 cells interacted more efficiently at 24 h than at 6 h after seizures, with a 3 fold increase of rolling cells and a 4 fold increase of firmly adherent cells at the later time point. The early arrest of PMN and later enhanced lymphocyte interactions are consistent with progression from acute to subacute inflammation during the 24 h period after SE-induced damage (FIG. 3A, B). Analysis of rolling velocities (Vroll) and the frequency distribution of Vroll in velocity classes is provided at FIG. 4 and Tables 3 and 4. No rolling or sticking of PMNs or Th1 cells was seen in normal mice not injected with pilocarpine. Interestingly, in vitro polarized Th2 cells did not roll or stick in brain vessels, suggesting that activated brain endothelium may preferentially recruit Th1 cells after seizures (FIG. 3A).

TABLE 4

Diameter, hemodynamics and rolling velocities in cerebral venules at 24 h post-SE[4]

| | Cell type | |
|---|---|---|
| | PMNs | Th1 cells |
| 24 HOURS post-SE Number of venules/animals | 7/4 | 4/3 |
| Diameter (μm) | 57 ± 25 | 71.6 ± 63.4 |
| $V_{fast}$ (μm/s) | 5528 ± 2141 | 4745 ± 117.4 |
| $V_m$ (μm/s) | 2792 ± 1061 | 2464 ± 61.5 |
| WSS (dyne/cm$^2$) | 10.4 ± 2.9 | 11.5 ± 10.4 |
| Median $V_{roll}$ (μm/s) | 35.5 | 46.2 |

[4]Parameters were calculated as described for Table 3.

Figure 3:
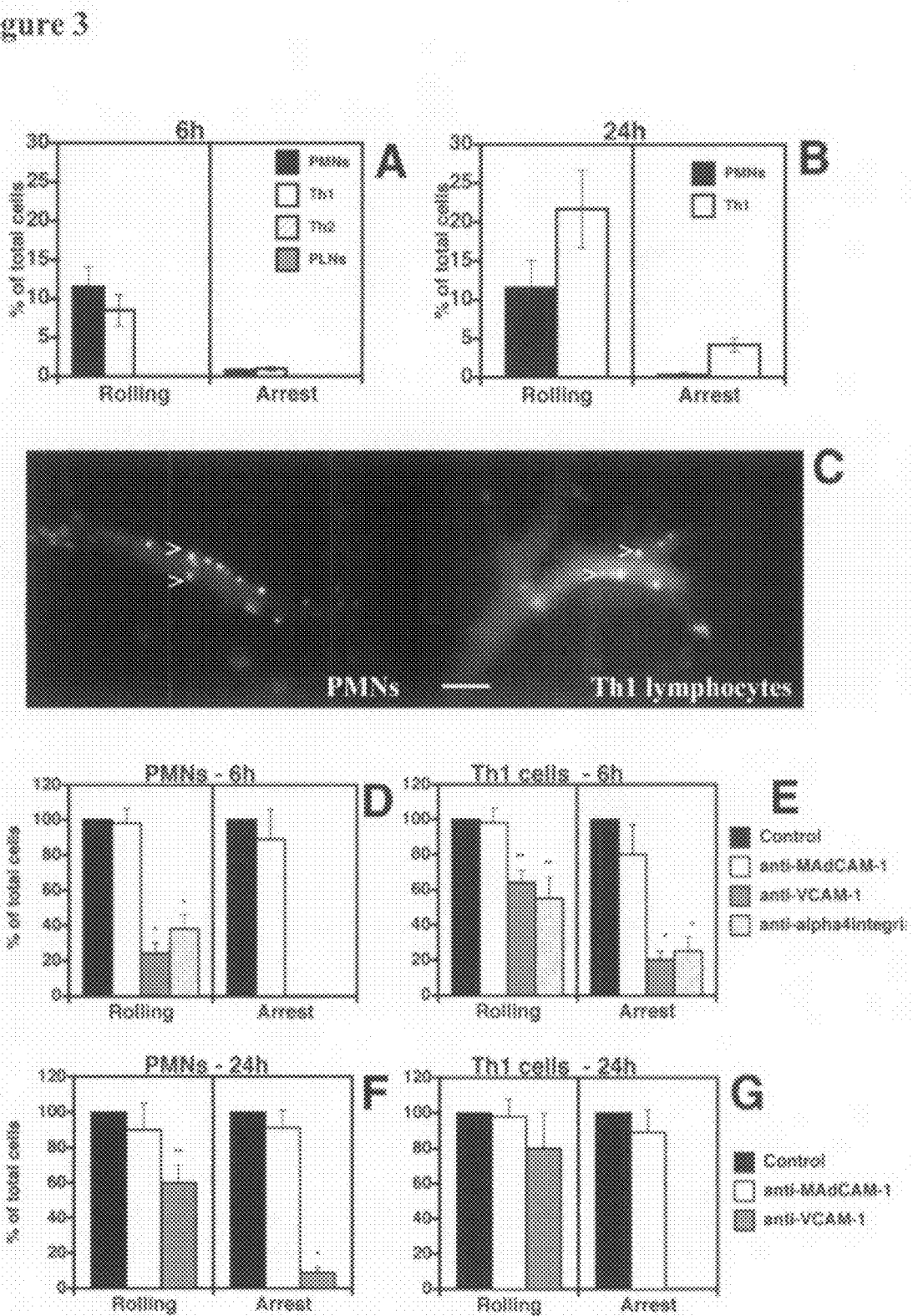

The induction of VCAM-1 suggested that leukocyte ligands, integrin α4β1 (receptor for VCAM1) might mediate leukocyte recruitment following seizure activity. Although classically associated with lymphocyte and monocyte adhesion, α4β1 also participates in PMN recruitment, and we first examined the effects of antibodies to VCAM-1 and α4 integrin on PMN interactions with the brain vasculature. As shown in FIG. 3, rolling interactions of PMNs after SE were dramatically inhibited by antibody blockade of VCAM-1 and α4 integrin (FIG. 3D). Moreover, these antibodies completely blocked sticking of PMN to vessels 6 h postseizure. Neutrophil sticking was also inhibited by 90% at the later time point, 24 h after SE (FIG. 3F). Anti-MAdCAM-1 mAb had no significant effect, excluding a role for α4β7 integrin and MAdCAM-1 adhesive interactions (FIG. 3F).

It has been previously considered that neutrophils do not express α4β1 integrin, a molecule implicated in the recruitment of monocytes, lymphocytes and eosinophils to sites of inflammation. However, in the last years consistent data from various laboratories demonstrate that neutrophils are indeed able to express the α4 integrin and use this alternative mechanism for adhesion and migration in experimental models of inflammation or in human disease.

TABLE 3

Diameter, hemodynamics and rolling velocities in cerebral venules at 6 h post-SE[3]

| | Cell type | | | |
|---|---|---|---|---|
| | PMNs | Th1 cells | Th2 cells | PLN cells |
| 6 HOURS post-SE Number of venules/ animals animals | 6/5 | 4/5 | 3/2 | 3/2 |
| Diameter (μm) | 72 ± 21 | 52 ± 34 | 68 ± 26 | 58 ± 44 |
| $V_{fast}$ (μm/s) | 4578 ± 1744 | 3469 ± 2779 | 3889 ± 1875 | 4421 ± 1988 |
| $V_m$ (μm/s) | 2303 ± 876 | 1786 ± 1356 | 1836 ± 885 | 2087 ± 938 |
| WSS (dyne/cm$^2$) | 7.2 ± 2.4 | 7.8 ± 0.8 | 8.7 ± 1.7 | 8.9 ± 1.8 |
| Median $V_{roll}$ (μm/s) | 40 | 18.2 | 0 | 0 |

[3]Venules were analyzed by individual velocity measurement of at least 20 consecutive non-interacting PLN cells, Th1, Th2 cells or PMNs in each venule. The velocity of the fastest cell in the sample ($V_{fast}$) was used to determine the mean blood flow velocity ($V_m$). Venular wall shear rate and wall shear stress (WSS) and the percentage of rolling and arrested cells were calculated as described at Materials and Methods section. The velocity of 10 rolling cells/venule was measured by digital frame-by-frame analysis of videotapes. $V_{roll}$ are presented as median. Data are arithmetic mean ± SD Rolling of Th1 cells was also significantly reduced by VCAM-1 or α4 blockade 6 h after SE but the inhibition was lower than that observed in PMNs (FIG. 3E). Arrest of Th1 cells was dramatically blocked at 6 h suggesting that VCAM-1 plays a critical role also for the early recruitment of lymphocytes. Notably, 95% of Th1 cell rolling was blocked by anti-PSGL-1, suggesting that PSGL-1 is a key molecule in the recruitment of lymphocytes after seizures. Sticking, but not rolling, of Th1 cells was totally blocked at 24 h, revealing a central role for VCAM-1 and PSGL-1 in the arrest of activated lymphocytes in CNS vessels post-SE (FIG. 3G). Taken together these results show that the integrin α4β1 and the selectin ligand PSGL-1 are critically involved in the recruitment of leukocytes to cerebral vessels following seizure activity. We reasoned that, if leukocyte recruitment is a significant contributor to the pathogenesis of seizure activity, then inhibition of α4β1 might alter the course of pilocarpine-induced SE and the subsequent development of chronic epilepsy.

Figure 5:
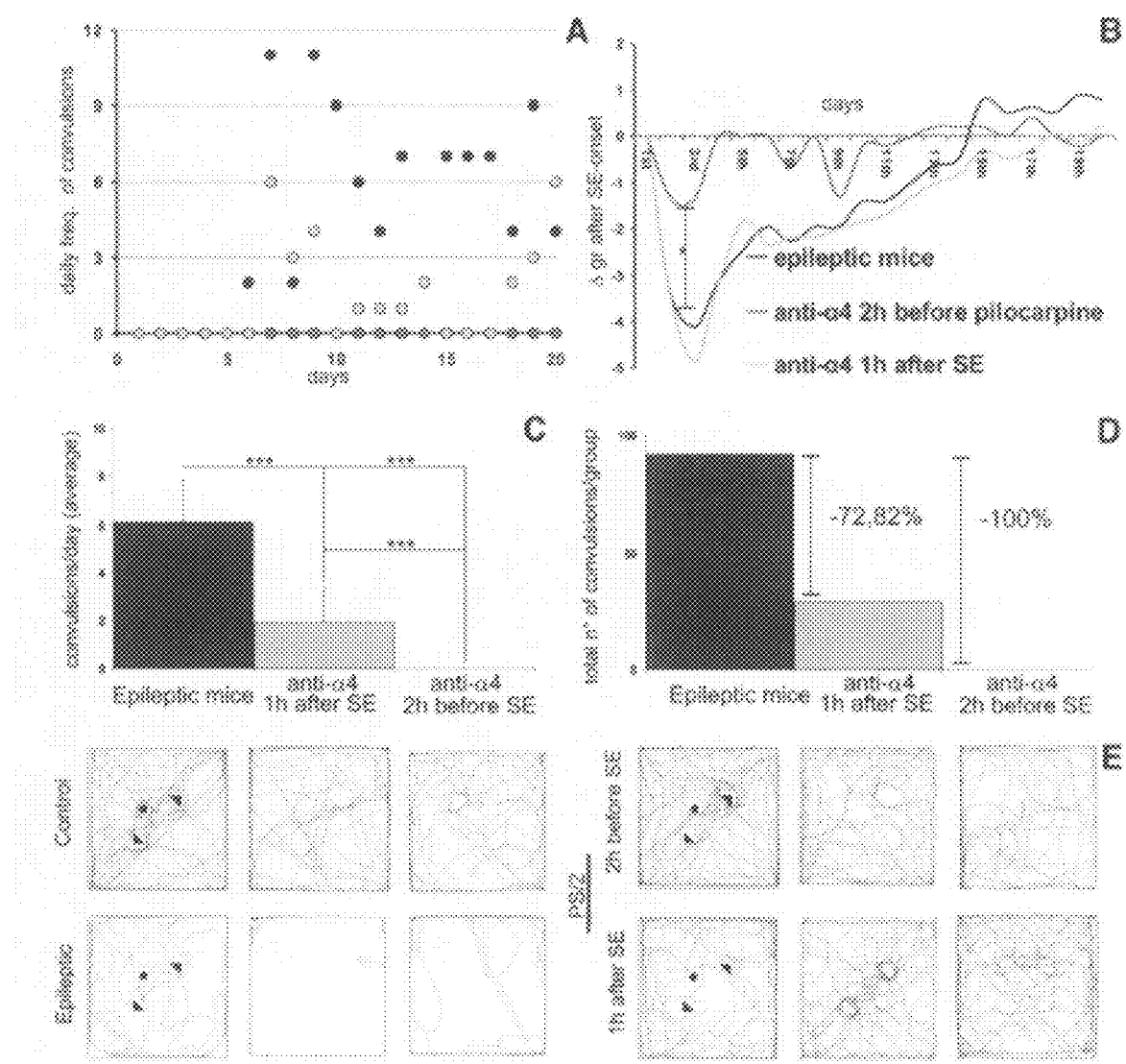
Figure 6:
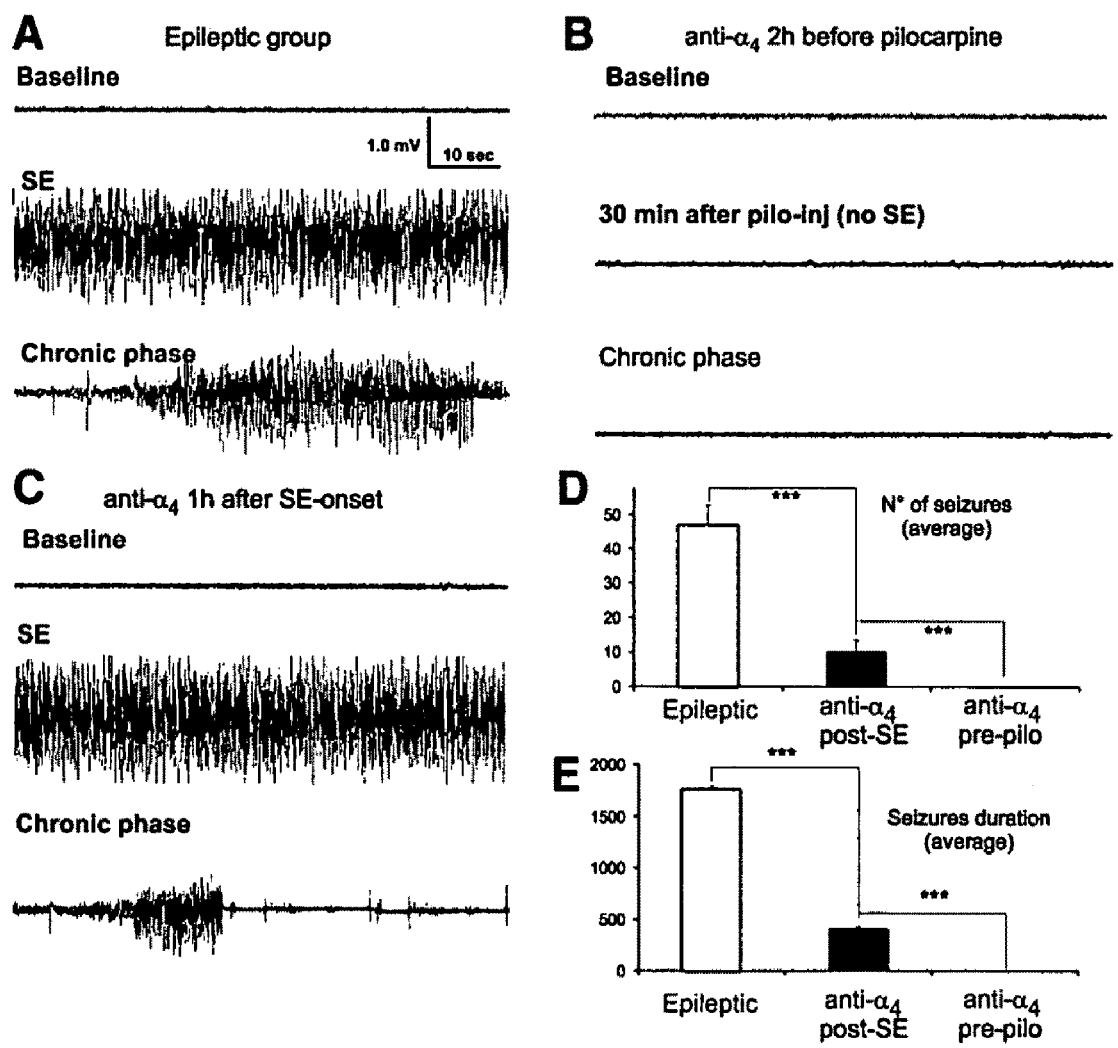

We next investigated the effects of α4 integrin blockade on SE and the evolution of epilepsy (FIGS. 5 and 6). To assess the ability of antibody therapy to alter the course of established SE and to influence the development of subsequent epilepsy, we induced seizure activity with pilocarpine and injected anti-α4 integrin mAb i.p. 1 hour after SE onset (stage 5 of Racine's Scale). Treatment after onset had no effect on the duration of the induced status epilepticus, but continuous video monitoring revealed a dramatic reduction in visible convulsions over the following 20 days (FIG. 5A, C, D). The frequency of convulsions over this period fell from 6.13±1.82 per day in the epileptic control group (SD, N=12 per group) to only 1.93±1.43 (P<0.001) in the anti-a4-treated mice (FIG. 5C).

EEG telemetry (FIG. 6A, C) confirmed the behavioral data by showing a drastic reduction in the number of abnormal electrical events and in total seizure time after SE in mice treated with anti-α4 integrin mAb when compared with control animals (FIG. 6D: Mean number of seizures/mouse: control epileptic group: 47±6 (SD, N=12 per group); anti-α4 integrin-treated group: 10±3, P<0.001; FIG. 6E: average seizure duration/mouse: epileptic: 1764±35 sec; anti-α4 integrin treatment: 409±21 sec, P<0.001). Mice treated with a control mAb showed no effect on the duration of SE and establishment of chronic disease. Cognitive evaluation based on enriched open-field exploration revealed that anti-α4 treated animals exhibited a slight reduction of exploration behavior compared to normal animals, but a significant preservation of the behavior compared to epileptic mice (FIG. 5E, Table 5).

TABLE 5

Enriched open field test in different experimental groups.
Episode Frequency (events/10 min)

| | | Mean | SEM |
|---|---|---|---|
| center | Controls | 27.3$^{a,e}$ | 3.8 |
| | Epileptics | 14$^{a,b,c}$ | 1.77 |
| | Anti-α4 2 h before SE | 26.1$^{b,d}$ | 2.54 |
| | Anti-α4 1 h after SE | 19.9$^{c,d,e}$ | 4.1 |
| inter-mediate | Controls | 135.9$^{f}$ | 6.2 |
| | Epileptics | 96.1$^{f,g,h}$ | 3.85 |
| | Anti-α4 2 h before SE | 127.7$^{g}$ | 4.74 |
| | Anti-α4 1 h after SE | 123.7$^{h}$ | 3.1 |

TABLE 5-continued

Enriched open field test in different experimental groups.
Episode Frequency (events/10 min)

| | | Mean | SEM |
|---|---|---|---|
| borders | Controls | 90.7$^{i}$ | 3 |
| | Epileptics | 36.5$^{i,j}$ | 4.2 |
| | Anti-α4 2 h before SE | 90.5$^{j}$ | 2.1 |
| | Anti-α4 1 h after SE | 57.3 | 1.9 |

$^a$p < .001;
$^b$p < .001;
$^c$p < .05;
$^d$p < .05;
$^e$p < .05;
$^f$p < .001;
$^g$p < .001;
$^h$p < .001;
$^i$p < .001;
$^j$p < .001

Cognitive evaluation was based on enriched open-field exploration. Epileptic animals have been previously reported to selectively decrement explorative behavior of new objects placed in the center of the arena. The cognitive evaluation revealed that anti-α4 treated animals before SE induction exhibited a normal exploration behavior compared to control animals (PBS injected mice). Mice treated 1 h after SE onset displayed a significant reduction of new objects exploration (center) when compared to control animals, but a significant improvement of the behavior when compared to epileptic animals. Post-hoc statistical values (ANOVA) are reported at the bottom of the Table.

The results obtained with anti-α4 integrin therapy were further confirmed by treating the mice with 150 µg anti-VCAM-1 mAb (M.K. 2.7)/day (12 mice/group), starting 1 h after the onset of SE (anti-VCAM-1 mAb administration was performed at the same time points as described for FIG. 5). The results clearly showed a dramatic reduction of the daily frequency of convulsions (from and 6.9±1.9 in the control epileptic group to 1.3±0.7 in the anti-VCAM-1 treated group) and total number of convulsions (80% reduction from 81.6 in the control epileptic group versus 16.8 in the ant-VCAM-1 treated group) over a period of observation of 30 days. Moreover, mice treated with anti-VCAM-1 mAb showed a significant preservation of normal behavior when compared with mice treated only with vehicle or with control mAb.

Figure 7:
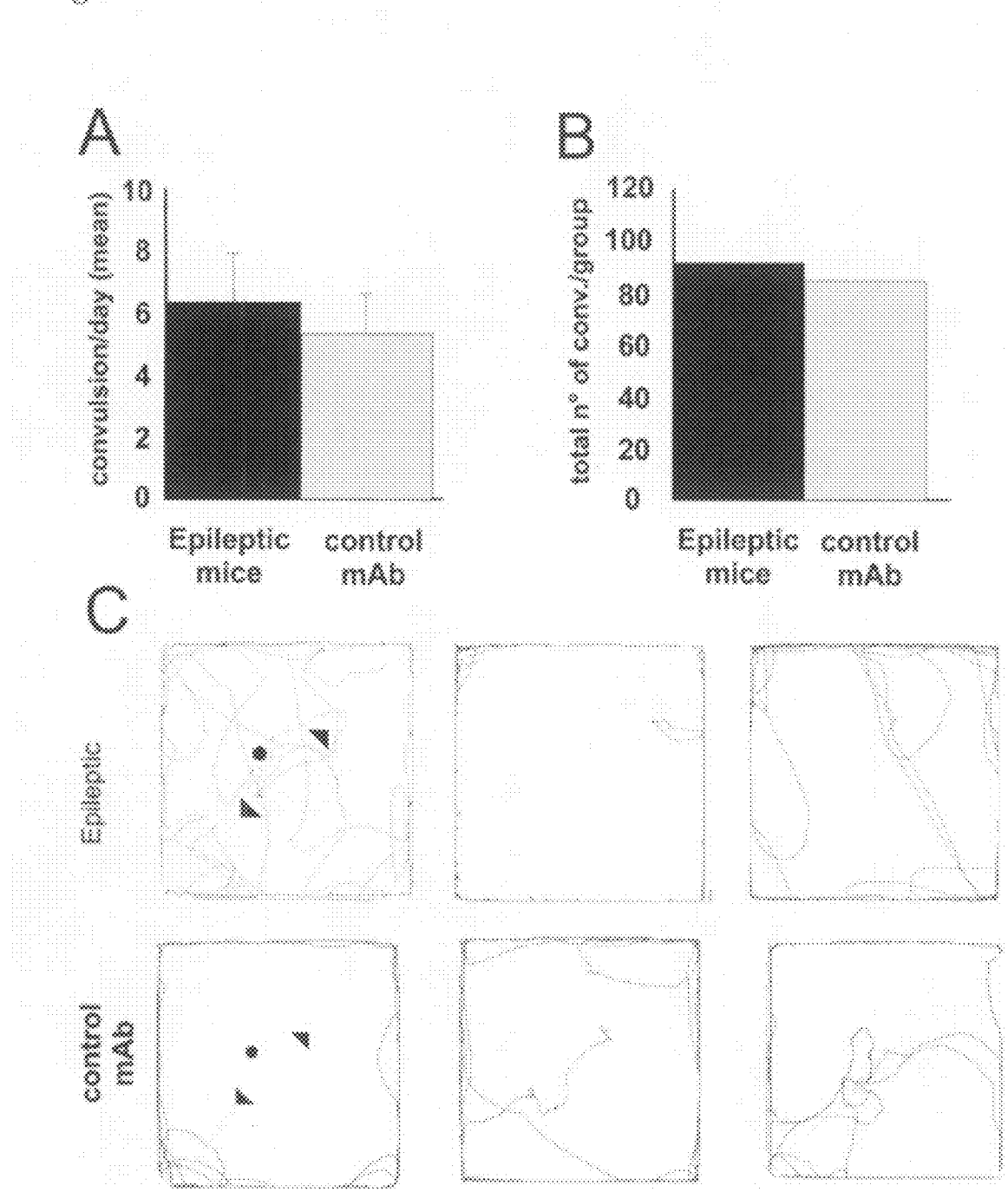

Finally, we evaluated the preventive effect of anti-α4 integrin mAb treatment. Strikingly, treatment with 200 µg anti-α4 integrin mAb i.p. 2 h before injection of pilocarpine completely prevented seizures (FIGS. 5 and 6). Behavioral observations included sporadic tremors and oral mastication (stage 2 of the Racine's Scale[18]) in anti-α4 integrin treated mice in the first hour after pilocarpine injection, but no further tremors and no convulsions were detected during the successive 20 days (FIG. 5 A, C, D). Moreover, anti-α4 integrin treated mice displayed no EEG alterations following pilocarpine-injection in the time-window analyzed (FIG. 6 A, B, D, E). α4 integrin blockade also prevented weight loss during the observation period (FIG. 5B). Mice treated with a control mAb showed no effect on the induction of SE and establishment of chronic disease (FIG. 7 and Table 6). Cognitive evaluation based on enriched open-field behavior revealed that animals receiving preventive treatment with anti-α4 integrin mAb behave like control (non-pilocarpine injected) mice with normal exploration of the central zone in a field characterized by new objects (FIG. 5E, Table 5).

Example 2

The increased expression of ICAM-1 on brain endothelium after seizures suggested that ICAM-1 and beta 2 integrins might mediate the leukocyte recruitment following seizure activity. To test this hypothesis, we examined the effects of antibodies to ICAM-1 and LFA-1 integrin on PMN interactions with the brain vasculature. As shown in FIG. 8, rolling interactions of PMNs after SE were significantly inhibited by blockade of ICAM-1 or LFA-1 integrin (inhibition of 60% of rolling for both mAbs). Moreover, the antibodies drastically blocked sticking of PMNs to vessels 6 h postseizure (blockade of 65% of adhesion by anti-alphaL mAb and of 62% by anti-ICAM-1 mAb). Neutrophil rolling and sticking was also strongly inhibited by anti-ICAM-1 mAb or anti-LFA-1 mAbs at the later time point, 24 h after SE. We conclude that LFA-1 integrin and ICAM-1 have an important role in the recruitment of PMNs to cerebral vessels following seizure activity.

Figure 9:
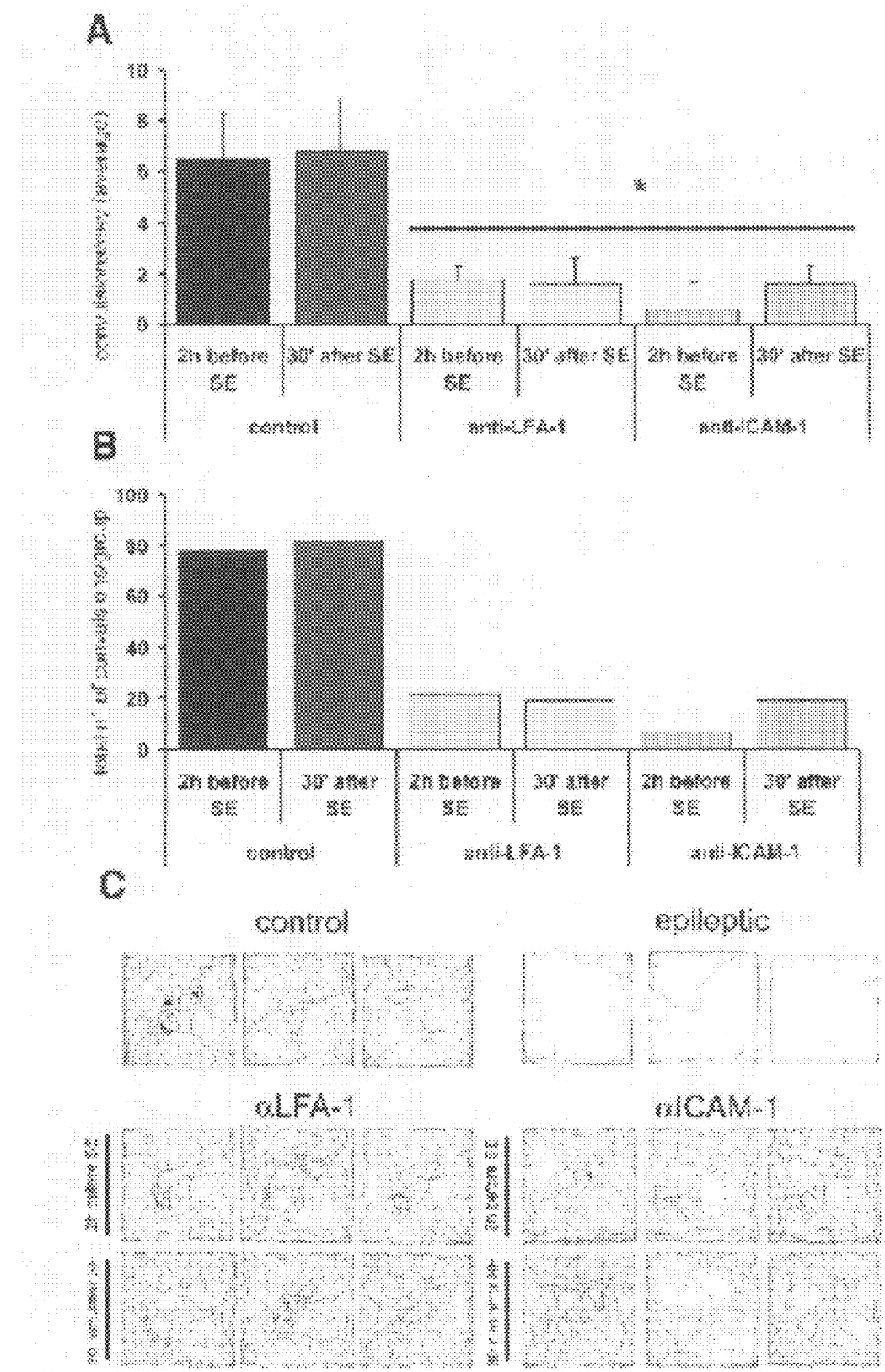

In mouse models of pilocarpine-induced status epilepticus (SE) and epilepsy, SE and repeated seizures induced expression of ICAM-1 on CNS vessels lasting for at least 30 days post SE (FIG. 2A). Therapeutic treatment of mice with anti-LFA-1 mAb (TIB 213) or with anti-ICAM-1 (Y.N. 1.7) leads to a drastic reduction in seizure activity (FIG. 9). The frequency of convulsions over the observation period fell from 6.8±2.1 per day in the epileptic control group (SD, N=10 per group) to only 1.6±1 (P<0.001) in the anti-LFA-1 treated mice and to 1.6±0.7 (FIG. 9A). In addition the total number of convulsions fell drastically from 78 in the epileptic control group to 22 in the anti-LFA-1 treated mice and to 19 in the anti-ICAM-1-treated group (FIG. 9B). Preventive administration of anti-LFA-1 therapy inhibits induction of SE and completely blocks recurrent seizures and development of epilepsy in 30-40% of animals. The frequency of convulsions over the observation period fell from 6.5±1.8 per day in the epileptic control group (SD, N=10 per group) to 1.8±0.5 (P<0.001) in the anti-LFA-1 treated mice and to 0.55 ±1.1 (FIG. 9A). In addition the total number of convulsions fell drastically from 82 in the epileptic control group to 19 in the anti-LFA-1 treated mice and to 7 in the anti-ICAM-1-treated group (FIG. 9B). Furthermore, anti-LFA-1 and anti-ICAM-1 treated mice showed a significant improvement of open-field exploration when compared to untreated epileptic-mice (FIG. 9C). Mice treated with a control mAb showed no effect on the induction of SE and establishment of chronic disease (FIG. 7 and Table 6). The results show a critical role for beta2 integrins and ICAM-1 in the induction of seizures and epilepsy.

TABLE 6

Enriched open field test in control mAb.
Episode Frequency (events/10 min)

|  |  | Mean | SEM |
|---|---|---|---|
| center | Epileptics | 14 | 1.77 |
|  | Control mAb | 12.1 | 1.3 |
| intermediate | Epileptics | 96.1 | 3.85 |
|  | Control mAb | 75.3 | 9.1 |
| borders | Epileptics | 36.5 | 4.2 |
|  | Control mAb | 31.1 | 4.7 |

Cognitive evaluation was based on enriched open-field exploration in epileptic versus control mAb-treated mice.

Example 3

The upregulation of P- and E-selectin on brain endothelium after seizures suggested that PSGL-1 and endothelial selectins mediate the leukocyte recruitment following seizure activity. We examined the effects of antibodies to PSGL-1, and P-selectin on PMN interactions with the brain vasculature. As shown in FIG. 8, rolling interactions of PMNs after SE were almost completely inhibited by blockade of ICAM-1 or LFA-1 integrin (inhibition of ~90% of rolling for both mAbs). Moreover, the antibodies abolished sticking of PMNs to vessels 6 h postseizure. Th1 cells rolling and sticking was also strongly inhibited by anti-PSGL-1 mAb or anti-P-selectin mAbs at 6 h after SE). We conclude that PSGL-1 and P-selectin are critically involved in the recruitment of leukocytes to cerebral vessels following seizure activity. We reasoned that, if leukocyte recruitment is a significant contributor to the pathogenesis of seizure activity, then inhibition of PSGL-1 will alter the course of pilocarpine-induced SE and the subsequent development of chronic epilepsy.

Although antibody should be excluded from the CNS by the BBB prior to status epilepticus, we could not rule out the formal possibility that anti-α4 or anti-αL treatment have direct effects on nervous tissue. To address this issue and to assess the role of additional adhesion mechanisms, we next evaluated the effects of genetic deficiency in the leukocyte-specific adhesion molecule, PSGL1. PSGL1 is a leukocyte mucin that participates in the recruitment of leukocytes to the inflamed brain by mediating leukocyte interactions with endothelial selectins. PSGL-1 binds both E- and P-selectin in vivo, and antibodies to PSGL-1 inhibit interactions of leukocytes with inflamed vessels in a number of animal models.

Two leukocyte-expressed α-1,3-fucosyltransferases (FucTs), FucT-VII and FucT-IV, modify PSGL-1 carbohydrates to generate functional selectin binding sites, and deficiency in these FucTs, like PSGL1 deficiency, inhibits leukocyte adhesion in experimental models models of inflammation. To assess the role of these mechanisms, we induced seizures and epilepsy in PSGL-1, FucT-VII or FucT-IV deficient mice. Continuous video monitoring and direct observations revealed a dramatic reduction in visible convulsions over the 30 days following pilocarpine administration in PSGL-1, FucT-IV and FucT-VII knockout mice (FIG. 10A, B). The frequency of convulsions over this period fell from 5.2±1.85 per day in the epileptic control group (N=10) to only 2.05±0.78 (P<0.001) in the PSGL-1$^{-/-}$ mice, and 0.4±0.55 (P<0.0001) in FucT-II$^{-/-}$ mice (FIG. 10A). No spontaneous recurrent convulsions were observed in FucT-VII$^{-/-}$ mice (FIG. 10A, B). The 30 day cumulative number of spontaneous recurrent convulsions per group was also dramatically decreased in PSGL-1$^{-/-}$ (–60.6%), FucT-IV$^{-/-}$ (–92.3%) and FucT-VII$^{-/-}$ (–100%) vs wild-type animals (FIG. 10B). The open field exploratory behaviour of PSGL-1$^{-/-}$, FucT-IV$^{-/-}$ and FucT-VIi$^{-/-}$ treated animals was also largely preserved (FIG. 10C, Table 7).

EEG telemetry (FIG. 11) confirmed the behavioral data by showing a drastic reduction in the number of abnormal electrical events and in total seizure time after SE in mice deficient of PSGL-1 when compared with control animals, and a complete absence of seizures in FucT-VII deficient mice was observed by telemetry (Mean number of seizures/mouse: control epileptic group: 44±8.9 (SD, N=10 per group); PSGL-1 deficient group: 5.3±2.2, P<0.0001; Average seizure duration/mouse: epileptic: 1652 sec; PSGL-1 deficient mice: 4.1±2.4 sec, P<0.001).

Taken together these results show that PSGL-1 and fucosyltransferase activity, previously described as a key element for the interactions mediated by selectins and mucin PSGL-1, are involved in the pathogenesis of seizures and epilepsy.

TABLE 7

Enriched open field test in mice deficient of PSGL-1 and FucTs.
Episode Frequency (events/10 min)

|  |  | Mean | SEM |
|---|---|---|---|
| center | Wild type | $11.1^{a,b,c}$ | 2.1 |
|  | PSGL-1$^{-/-}$ | $22.3^{a}$ | 2.4 |
|  | FucT-IV$^{-/-}$ | $28.2^{b}$ | 3.5 |
|  | FucT-VII$^{-/-}$ | $27.8^{c}$ | 3.1 |
| intermediate | Wild type | $62.4^{d,e,f}$ | 5.9 |
|  | PSGL-1$^{-/-}$ | $96.1^{d,g,h}$ | 3.8 |
|  | FucT-IV$^{-/-}$ | $125.1^{e,g}$ | 3.6 |
|  | FucT-VII$^{-/-}$ | $130.9^{f,h}$ | 3.9 |
| borders | Wild type | $25.9^{i,j,k}$ | 3.4 |
|  | PSGL-1$^{-/-}$ | $56.5^{j}$ | 3.1 |
|  | FucT-IV$^{-/-}$ | $89.4^{j}$ | 2.4 |
|  | FucT-VII$^{-/-}$ | $67.4^{k}$ | 1.5 |

$^a$ $p < .001$;
$^b$ $p < .001$;
$^c$ $p < .001$;
$^d$ $p < .001$;
$^e$ $p < .001$;
$^f$ $p < .001$;
$^g$ $p < .05$;
$^h$ $p < .05$;
$^i$ $p < .01$;
$^j$ $p < .01$;
$^k$ $p < .01$

Cognitive evaluation was based on enriched open-field exploration in wild-type versus knockout mice. Post-hoc statistical values (ANOVA) are reported at the bottom of the Table.

The ability of anti-a4 treatment and PSGL-1/FucT deficiency to inhibit not only the development of recurrent seizures, but also the initial seizure activity is surprising. Pilocarpine-induced vascular adhesion molecule expression is reduced if seizures are prevented pharmacologically with diazepam, suggesting that electrical activity stimulates the vascular response. On the other hand, prevention of convulsant activity by anti-α4 treatment or by PSGL-1 or FucT deficiency in the current study (and also by interference with ICAM-1 or β2 integrins interactions required for leukocyte-vascular interaction in the CNS) strongly suggests that leukocyte recruitment (at least to the CNS vasculature) may enable or amplify the electrical hyperactivity required for seizures. One possibility is that there is a critical positive feedback loop between leukocyte recruitment, vascular changes and CNS electrical hyperactivity. In this model, a low level of constitutive leukocyte interactions with the vessel wall is required in combination with a suboptimal stimulus to CNS hyperactivity to initiate the process, with a feedback between inflammatory vascular changes, additional leukocyte-mediated inflammatory changes, and increasing CNS activity being associated with and required for initiation of convulsions. Chronic expression of VCAM-1 after seizures suggests that leukocyte recruitment may continue, contributing to neuroinflammation and potentially to brain damage that could explain, at least in part, the evolution to chronic epilepsy. Thus, we hypothesize that a cycle of seizure-induced inflammation and inflammation-mediated cortical stimulation and ultimately damage may amplify initial effects, leading to SE and to recurrent seizure activity.

We also show that transfused Th1 cells enter into the brain early post seizures. Th1 cells are detected in brain tissue early in the development of autoimmune diseases of the brain where they are responsible of the induction of a chronic inflammatory process. The lack of interactions between Th2 cells and brain endothelium suggest that, at least in early phases of inflammation after seizures, Th1 might be preferentially recruited. Other leukocyte subpopulations such as monocytes might have a role in the induction of seizures and/or establishment of chronic disease, as well, since α4β1-VCAM-1 have been shown to have a central role for monocyte adhesion to inflamed endothelium in vitro and in vivo. Chronic expression of ICAM-1 and VCAM-1 after seizures suggests that leukocyte recruitment may continue, contributing to neuroinflammation and potentially to brain damage that could explain; at least in part, the evolution to chronic epilepsy. A cycle of seizure-induced inflammation and inflammation-mediated cortical stimulation and ultimately damage can amplify the effects, leading to SE and to recurrent seizure activity.

The currently available pharmacological treatments for epilepsy inhibit neuronal excitability but do not address inciting pathogenic mechanisms. Involvement of inflammatory cells in the etiology and pathogenesis of seizures has been the subject of conjecture, but has not been examined experimentally. We show here that multiple mechanisms involved in the multistep process of leukocyte-CNS vascular interactions and recruitment can be targeted to alter seizure activity, supporting the hypothesis that it is blockade of leukocyte recruitment that is responsible for the therapeutic effect. Our results demonstrate leukocyte recruitment as a component of the pathogenesis of epilepsy, and demonstrate that targeting α4 integrin, beta 2 integrins, VCAM-1, ICAM-1, PSGL-1 and Fucosyltransferases prevents and treats epilepsy in mouse models. A humanized anti-α4 integrin antibody (Natalizumab/Tysabri) used for treatment. of multiple sclerosis, a human inflammatory disease of the CNS, is already available for clinical trials. Although adverse reactions have been encountered after prolonged Natalizumab treatment, apparently as a result of immunosuppression, this is unlikely to occur with short periods of anti-leukocyte adhesion therapy after seizure activity. In addition, a recombinant immunoglobulin chimeric form of PSGL1, YSPSL (rPSGL-Ig) is currently urider evaluation for the prevention of graft dysfunction in kidney transplantation, and a humanized anti-LFA-1 integrin antibody (Efalizumab/Raptiva) is currently used for psoriasis. Anti-adhesion therapies can also help prevent the occurrence of epilepsy following brain insults associated with inflammation such as traumatic brain injury, for instance in military personnel in war zones, where seizures and epilepsy present a significant health problem.

Moreover, our results show that brain endothelium expresses adhesion molecules either after pilocarpine-induced seizures or kainic acid-induced seizures (FIG. 15). Thus, independently on the experimental model of epilepsy, BBB becomes activated after seizures and expresses adhesion molecules, which can recruit leukocytes from the blood stream inducing BBB increased permeability and neuronal damage.

In conclusion, these results revolutionize understanding of the pathogenesis of epilepsy and seizures, showing a key role for leukocyte recruitment and demonstrating that anti-leukocyte adhesion therapy has preventive as well as therapeutic effects in this debilitating disease.

Materials and Methods

Reagents. MAbs anti-α4 integrin PS/2, anti-VCAM-1 MK 2.7, anti-ICAM-1 YN 1.1.7.4, anti-MAdCAM-1 were from American Type Culture Collection or were produced in our lab.

Induction of seizures and epilepsy. The study was based on young C57BU6 male mice (30-50 days of age, weight range: 19-23 gr) maintained on a 12 h light/dark inverted schedule, with access to food and water ad libitum, and habituated to the experimenters for at least two weeks prior to the procedures employed in the present study. The experiments received authorization from the Italian Ministry of Health, and were conducted following the principles of the NIH Guide for the Use and Care of Laboratory Animals, and the European Community Council (86/609/EEC) directive. Thirty minutes before application of pilocarpine, the animals were pretreated with methyl-scopolamine (1 mg/kg, i.p.; Sigma, Germany). Subsequently, mice were injected i.p. with 300 mg/kg pilocarpine (Sigma, Germany) diluted in 0.01 M phosphate-buffered saline, pH 7.4 (PBS). For status epilepticus blockade mice were injected with Diazepam i.p. (3 mg/Kg) 20 min before pilocarpine administration.

MRI (magnetic resonance imaging) analysis. Evaluation of FeO labeled leukocyte migration. Murine Th1 cells or PMNs freshly isolated from bone marrow have been seeded in a 24 well plate at $5 \times 10^6$ cells/ml/ well in growth medium, and labeled with iron particles (Resovist, Schering AG, solution containing 540 mg ferucarbotran equal to 28 mgFe/ml) at a concentration of 100 µg/ml. After 14-16 h incubation, cells have been washed 3 times in D-PBS; cell viability has been determined by staining with Trypanblue, and incorporation of iron particles was evaluated by staining of cytospins by Mellory (Prussian Blue). PMNs were injected IV into mice 1h post-SE onset, while Th1 cells were injected 24 h post-SE onset. After 18-24 h mice were perfused with 4% paraformaldehyde and were observed by MRI using the transmitter-receiver coil configuration described before. Gradient Echo images were acquired using the following parameters: TR=350 ms; TE=12 ms; matrix size=256×256; FOV=2× 2cm2; NEX=12; slice thickness=2; number of slices=10.

Behavioral assessment. Cognitive alterations, evaluated by enriched environment exploration behavior, were recorded by Ethovision 3.0 (Noldus Information Technology, Wageningen, the Netherland). Briefly, animals were placed for the first time for 10 min in a square (150×150 cm), with three different colored objects in the center. Time spent in proximity of square wall (W), central objects (C) and intermediate zone (I) was used to quantify explorative behavior. Before testing the behavioural phenotype, studies were carried out in order to evaluate if the treatment had any effect on the motor coordination and strength. The animals were thus tested for the motor coordination by Rota-Rod (Ugo Basile, Varese, Italy), while motor strength was assessed by the Grip Strength Meter (Ugo Basile).

Telemetry EEG. Seizures onset, severity and duration were assessed by electroencephalogram (EEG) acquisition system using telemetric technology (Dataquest® A.R.T. Data Acquisition 3.0 for telemetry systems, Data Sciences International, Arden Hills, Minn., USA). We recorded 24 h/day for 20 consecutive days, EEG, body temperature and movements for each single animal.

PMN preparation. Mouse bone marrow PMNs were isolated from femurs and tibias as previously described. Briefly marrow cells were flushed from the bones using Hank's balanced salt solution without $Ca^{2+}$ and $Mg^{2+}$. After hypotonic lysis of erythrocytes cells were loaded on top of a Percoll discontinuous density gradient and, after centrifugation cells were harvested and washed before use.

Production of murine Th1 and Th2 cells. Naïve CD4+ T cells were positively selected from spleens and lymph nodes of C57Bl/6 mice by anti-CD4-coated magnetic microbeads and by anti-CD62-coated magnetic microbeads (Miltenyi-Biotec GmbH). Obtainment of Th1 and Th2 cells was performed as previously described. The phenotype of Th1 and Th2 cell lines was determined by intracytoplasmic staining for IFN-γ and IL-4.

In vivo staining of endothelial adhesion molecules. MAbs anti-VCAM-1, anti-ICAM-1, anti-MAdCAM-1, anti-P-selectin, anti-E-selectin and isotype-matched control antibody (anti-human Ras) with Alexa Fluor 488 (Molecular probes) and injected intravenously. Cerebral vessels were visualized using the intravital microscopy setting as previously described.

Patients. All human samples were obtained from the Department of Medicine and Public Health of the Insubria University, Varese, Italy (O.A.). 10 long-term epileptics with no concurrent inflammatory brain diagnoses, 10 age-matched controls, and 10 patients with non inflammatory neurological diseases (almost all diagnosed with Parkinson disease) were included in the study. All patients considered in this study died of non-inflammatory brain diseases.

Statistics: Statistical analysis of the results, was performed by using Prism software. A two-tailed Student's t test was employed for statistical comparison of two samples. Multiple comparisons were performed employing Kruskall-Wallis test with the Bonferroni correction of P or by using ANOVA. Velocity histograms were compared using Man-Whitney U-test and Kolmogorov-Smirnov test. Differences were regarded significant with a value of $P<0.05$.

Immunofluorescence. Free floating sections were washed in PBS at room temperature and permeabilized for 1 hour in PBS containing 0.3% Triton X-100, 1% bovine serum albumin and 2% normal goat serum, the same solution was used to dilute the antibodies. Subsequently, sections were incubated overnight with rat anti-mouse CD 3 (1:400, Serotec, Oxford, UK) or rat anti-mouse Gr-1 (1:400, Serotec, Oxford, UK). After washes, sections were then incubated in fluorescein (FITC) conjugated affinity purified goat anti-rat IgG (1:100; Jackson Laboratories, INC; Baltimore, Pa.) or goat anti-rabbit IgG (1:200; Jackson Laboratories) for two hours at room temperature. Finally, sections were collected on plysine-coated slides, mounted with with Fluorescent Mounting Medium (DAKO, Milan, Italy) and observed with a Zeiss LSM 510 confocal microscope. All images for publication were composed in Adobe Photoshop software (version 7.0; Adobe Systems, Mountain View, Calif.). Sections treated as above, but in the absence of the primary or secondary antibody were used as control.

Immunohistochemistry. Paraffin sections of human brains (see Table 1) were processed for immunohistochemistry using the Labeled Polymer method. Briefly, deparaffinized sections were rehydrated and endogenous peroxidase activity was quenched by 15-min incubation in a solution of 3% hydrogen peroxide in methanol. After washing in 0.05 M Tris-HCl buffer (pH 7.6) sections were incubated for 30 min at room temperature with the following primary antibodies: anti-human CD45, Leucocyte Common Antigen (1:100, Dako), anti-human CD3 (1:100, Novocastra Laboratories Ltd. UK), anti-human Myeloperoxidase (1:500, Dako). Immunoreaction was revealed by incubating sections with immunoglobulins conjugated to peroxidase labelled-dextran polymer (Envision+™, Dako, Milan, Italy) for 30 min at room temperature. Finally, all sections were reacted with 0.05 M 3,3-diaminobenzidine tetrahydrochloride for 3-5 min and counterstained with hematoxylin. Sections were then dehydrated, mounted and observed in a Olympus BX51 photomicroscope equipped with a KY-F58 CCD camera (JVC).

Intravital microscopy. C56Bl/6 young males were purchased from Harlan-Nossan (Udine,. Italy) and were housed and used according to current European community rules for the usage of laboratory animals. At 6 h or 24 h post seizure induction with pilocarpine, mice were anesthetized by intraperitoneal injection (10 ml/kg) of physiologic saline containing with ketamine (5 mg/ml) and xylazine (1 mg/ml). The recipient was maintained at 37° C. by a stage mounted strip heater Linkam CO102 (Olympus). A heparinized PE-10 polyethylene catheter was inserted into the right common carotid artery toward the brain. In order to exclude from the analysis the non cerebral vessels, the right external carotid artery and pterygopalatine artery, a branch from the internal carotid, were ligated. The scalp was reflected and the skull was bathed with sterile saline, and a 24mm×24mm coverslip was applied and fixed with silicon grease. A round chamber with 11 mm internal diameter was attached on the cover slip and filled with water.

The preparation was placed on an Olympus BX50WI microscope and a water immersion objective with long focal distance (Olympus Achroplan, focal distance 3.3 mm, NA 0.5∞) was used. Blood vessels were visualized by using fluorescent dextrans: 3mg of FITC-dextran (148 kD; Sigma) and/or 6 mg of TRITC-dextran (155 kD; Sigma) were diluted in 0.3 ml sterile physiologic saline and centrifuged for 5 min at 14,000 g (each mouse received 0.05 ml supernatant). $2.5 \times 10^6$ fluorescent labeled cells/condition were slowly injected into the carotid artery by a digital pump at a flow rate of 0.13-1 μl/s. Leukocytes were labeled with either green CMFDA (5-chloromethylfluorescein diacetate) (Molecular probes) or orange CMTMR (5-(and -6)-(((chloromethyl)benzoyl) amino)tetramethylrhodamine) (Molecular Probes). The images were visualized by using a silicon-intensified target videocamera (VE-1000 SIT, Dage MTI, Michigan, Ill.) and a Sony SSM-125CE monitor. Recordings were digitalized and stored on videotapes employing a digital VCR (Panasonic NV-DV10000). The recordings were made during the injection of the cells and for a few minutes after the injection was ended.

Video analysis was performed by playback of digital videotapes in real time or at reduced speed, and frame by frame. Vessel diameter (D), hemodynamic parameters and the velocities of rolling were determined by using the NIH Image 1.62 software. The velocities of ≧20 consecutive freely flowing cells/venule were calculated, and from the velocity of the fastest cell in each venule ($V_{fast}$), we calculated the mean blood flow velocities ($V_m$): $V_m = V_{fast}/(2-\epsilon^2)$ where $\epsilon$ is the ratio of the lymphocyte diameter to vessel diameter. The wall shear rate (γ) was calculated from $\gamma = 8 \times V_m/D$ $(s^{-1})$, and the shear stress (τ) acting on rolling cells was approximated by γ×0.025 $(dyn/cm_2)$, assuming a blood viscosity of 0.025 Poise. Lymphocytes were considered as rolling if they traveled at velocities below $V_{crit}$ ($V_{crit} = V_m \times \epsilon \times (2-\epsilon)$). Lymphocytes that remained stationary on venular wall for ≧30 s were considered adherent. At least 150 consecutive cells/venule were examined. Rolling and arrest fractions were determined as the percentage of cells that rolled or firmly arrested within a given venule in the total number of cells that enter that venule during the same period.

Determination of BBB permeability. MRI experiments were performed using a Bruker Biospec Tomograph equipped with an Oxford, 33-cm-bore. Animals were anaesthetized and placed in prone position into a 7.2 cm transmitter birdcage coil. The signal was acquired by a 1.5 cm actively decoupled surface coil. The tail vein was cannulated for injection of contrast agent (Magnevist, Schering 100 micromol/kg). Multislice, T1-weighted Spin Echo images were acquired before and up to 24 min after injection of Magnevist. The acquisition parameters were: TR=350 ms; TE=14.4 ms; matrix size=128×128; FOV=3×3 cm2. Twelve contiguous, 1 mm-thick slices were acquired to cover the whole-brain.

In vitro adhesion assays. Adhesion was performed on purified integrin ligands as reported29. Blood leukocytes were isolated after hypotonic lysis of erythrocytes. Adhesion assays were performed on eighteen well glass slides coated with VCAM-1. Cells were treated with pilocarpine at different concentrations and time points. After 20 min, slides were washed, fixed and computer-assisted enumeration of bound cells was performed as described.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

What is claimed is:

1. A method of preventing seizures in an individual mammal that has epilepsy, said method comprising:
    administering to said individual mammal an effective amount of an antibody specific for an α4 integrin to inhibit the recurrence of seizures.

* * * * *

UNITED STATES PATENT AND TRADEMARK OFFICE
CERTIFICATE OF CORRECTION

PATENT NO. : 7,682,613 B2 Page 1 of 1
APPLICATION NO. : 11/811245
DATED : March 23, 2010
INVENTOR(S) : Paolo Francesco Fabene It is certified that error appears in the above-identified patent and that said Letters Patent is hereby corrected as shown below:

On the Title page of the patent in the application data:

- Item (22) Filed: Jun. 6, 2007, the date "Jun. 6, 2007" should read --Jun. 7, 2007--

Signed and Sealed this

Thirteenth Day of July, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,682,613 B2 | Page 1 of 1 |
| APPLICATION NO. | : 11/811245 | |
| DATED | : March 23, 2010 | |
| INVENTOR(S) | : Fabene et al. | |

It is certified that error appears in the above-identified patent and that said Letters Patent is hereby corrected as shown below:

Column 1, line 11-13 should read:

-- FEDERALLY-SPONSORED RESEARCH OR DEVELOPMENT
This invention was made with Government support under contracts GM037734 and AI047822 awarded by the National Institutes of Health. The Government has certain rights in this invention. --

Signed and Sealed this
Twenty-fourth Day of April, 2012

David J. Kappos
*Director of the United States Patent and Trademark Office*